(12) United States Patent
Lafdi et al.

(10) Patent No.: US 8,764,696 B2
(45) Date of Patent: Jul. 1, 2014

(54) MEDICAL DRAINAGE DEVICES WITH CARBON-BASED STRUCTURES FOR INHIBITING GROWTH OF FIBROBLASTS

(75) Inventors: Khalid Lafdi, Dayton, OH (US); Edward J. Timm, Webster Groves, MO (US)

(73) Assignee: Mobius Therapeutics, Inc., St. Louis, MO (US)

( * ) Notice: Subject to any disclaimer, the term of this patent is extended or adjusted under 35 U.S.C. 154(b) by 257 days.

(21) Appl. No.: 12/816,840

(22) Filed: Jun. 16, 2010

(65) Prior Publication Data

US 2011/0144559 A1 Jun. 16, 2011

Related U.S. Application Data

(60) Provisional application No. 61/187,533, filed on Jun. 16, 2009.

(51) Int. Cl.
A61M 5/00 (2006.01)

(52) U.S. Cl.
USPC ............................................................ 604/8

(58) Field of Classification Search
USPC ............................................................ 604/8
See application file for complete search history.

(56) References Cited

U.S. PATENT DOCUMENTS

| | | | |
|---|---|---|---|
| 4,398,910 A | | 8/1983 | Blake et al. |
| 6,450,984 B1 * | | 9/2002 | Lynch et al. ................. 604/8 |
| 6,689,085 B1 * | | 2/2004 | Rubenstein et al. ............. 604/9 |
| 7,220,238 B2 * | | 5/2007 | Lynch et al. ................ 604/8 |
| 7,355,216 B2 * | | 4/2008 | Yang et al. ................... 257/200 |
| 2002/0026200 A1 * | | 2/2002 | Savage ....................... 606/108 |
| 2003/0167031 A1 * | | 9/2003 | Odland ............................ 604/8 |
| 2003/0220603 A1 * | | 11/2003 | Lynch et al. .................... 604/8 |
| 2003/0236483 A1 * | | 12/2003 | Ren .................................. 604/8 |
| 2004/0210185 A1 * | | 10/2004 | Tu et al. ........................ 604/27 |
| 2004/0225250 A1 * | | 11/2004 | Yablonski ..................... 604/8 |
| 2005/0277864 A1 * | | 12/2005 | Haffner et al. ................. 604/8 |
| 2005/0283108 A1 * | | 12/2005 | Savage ............................. 604/8 |
| 2006/0015089 A1 * | | 1/2006 | Meglin et al. .............. 604/890.1 |
| 2006/0093642 A1 * | | 5/2006 | Ranade ....................... 424/423 |
| 2006/0173397 A1 * | | 8/2006 | Tu et al. ........................ 604/8 |
| 2006/0204738 A1 * | | 9/2006 | Dubrow et al. ............ 428/292.1 |
| 2007/0276316 A1 * | | 11/2007 | Haffner et al. ................. 604/8 |
| 2007/0282247 A1 * | | 12/2007 | Desai et al. .................... 604/19 |
| 2007/0293807 A1 * | | 12/2007 | Lynch et al. .................. 604/8 |
| 2008/0009781 A1 * | | 1/2008 | Anwar et al. .................. 604/8 |
| 2008/0015488 A1 * | | 1/2008 | Tu et al. ......................... 604/8 |
| 2008/0051691 A1 * | | 2/2008 | Dragoon et al. ............... 604/8 |

* cited by examiner

*Primary Examiner* — Susan Su
*Assistant Examiner* — Guy K Townsend
(74) *Attorney, Agent, or Firm* — Polsinelli PC

(57) ABSTRACT

Drainage devices for draining a fluid from a patient during treatment of a medical condition body are disclosed. The drainage devices comprise a body defining at least one conduit through the body from a distal end of the body to a proximal end of the body. The body comprises at least one carbon-based structure configured to inhibit growth of fibroblasts in the conduit when the fluid flows through the conduit. Example embodiments of the drainage device may include an ophthalmic shunt, a hydrocephalus shunt, an artificial mesh, an arteriovenous shunt, a thoracic catheter, and a central venous access device.

25 Claims, 18 Drawing Sheets

MEDICAL DRAINAGE DEVICES WITH CARBON-BASED STRUCTURES FOR INHIBITING GROWTH OF FIBROBLASTS

CROSS-REFERENCE TO RELATED APPLICATIONS

The present application claims priority under 35 U.S.C. §119(e) to U.S. Provisional Application Ser. No. 61/187,533, filed Jun. 16, 2009.

FIELD

This application relates to drainage devices for draining fluid from the body during treatment of a medical condition, and more particularly to drainage devices having carbon-based structures for preventing or inhibiting growth of fibroblasts during drainage procedures.

BACKGROUND

Drainage devices such as shunts and catheters, for example, commonly are used by medical professionals to drain fluid from a patient's body. In some situations, fluid may need to be drained from operative sites or from wounds. Fluid drainage also may be performed to treat medical conditions for which the fluid causes abnormal pressures, whereby the drainage relieves the abnormal pressure.

Glaucoma, for example, is a disease of the major optic nerve, the nerve responsible for receiving light from the retina and transmitting impulses to the brain to be perceived as an image. Glaucoma is characterized by a particular pattern of progressive damage to the optic nerve that generally begins with a subtle loss of peripheral vision. If glaucoma is not diagnosed and treated, it can progress to loss of central vision and ultimately to blindness. Glaucoma usually is associated with elevated pressure in the eye. Generally, it is this elevated eye pressure that leads to loss of sight through progressive damage to the optic nerve. Thus, in the treatment of glaucoma the principal objective is the lowering of intraocular pressure in the eye.

Numerous therapies using ophthalmic shunts as ocular drainage devices have been developed for treating glaucoma. Use of the ophthalmic shunts decreases the intraocular pressure by promoting fluid flow of aqueous humor from the eye. Typically, ophthalmic shunts are made from a silicone material that provide a passageway or multiple conduits adapted for permitting the evacuation of aqueous humor from the eye. But it has been found that ophthalmic shunts made from silicone can promote fibroblast growth around the ophthalmic shunt and that the fibroblasts can either completely encapsulate the shunt or block the one or more passageways of the shunt to prevent fluid from being evacuated from the eye. And regardless of the choice of material for an ophthalmic shunt, the ophthalmic shunt must be both conformal and pliable to be suitable for the delicate procedure of draining ocular fluid.

Among the many types of drainage devices, the problem of fibroblast growth is not unique to ophthalmic shunts. Fibroblast growth also can adversely affect other types of drainage devices, such as hydrocephalus shunts, arteriovenous shunts, thoracic catheters, and central venous access devices. The adverse effect is quite similar in all examples. That is, in these examples the fibroblasts may prevent fluid flow or fluid evacuation from the drainage devices. Likewise, even drainage devices that are embolic and used with long-term indwelling catheters can clog or become occluded as a result of fibroblast growth.

Accordingly, there is a need in the art for drainage devices that are made from materials capable of inhibiting fibroblast proliferation, devices that are specially configured for their specific application, or devices comprising both fibroblast-inhibiting materials and special configurations, to inhibit or completely prevent fibroblast growth around or within the drainage device.

SUMMARY

Embodiments described herein relate to drainage devices for draining a fluid from a patient during treatment of a medical condition body. The drainage devices comprise a body defining at least one conduit through the body from a distal end of the body to a proximal end of the body. The body comprises at least one carbon-based structure configured to inhibit growth of fibroblasts in the conduit when the fluid flows through the conduit.

In an example embodiment of the drainage device, an ophthalmic shunt may include a body defining at least one conduit in communication with a proximal opening and an opposing distal opening. In example embodiments, the body may be tubular or may comprise a plurality of flutes meeting at a central stem. The body may be made from an electrically conductive substrate with a vapor deposition of pure carbon or a carbon-based structure applied on the substrate in an intimately conformal manner.

In one embodiment of the drainage device, a hydrocephalus shunt may include a tubular body defining a closed distal end and at least one conduit in communication with a proximal opening. The tubular body may further define a plurality of openings in communication with at least one conduit, wherein the tubular body is made from a carbon-infused elastomer.

In another embodiment of the drainage device, an artificial mesh may include a body made from a carbon substrate having a plurality of carbon nanotubes with each of the plurality of carbon nanotubes defining a conduit in communication with a proximal opening and an opposing distal opening. The body may further define a rectangular configuration adapted to be maintained over a trabeculotomy performed on a patient, wherein the body is made from a carbon substrate that is coated or plated with a metal substance, such as gold, silver, nickel, titanium, tantalum, niobium, and alloys thereof.

In yet another embodiment of the drainage device, an arteriovenous shunt may include a body defining a proximal end and a distal end with a plurality of longitudinal flutes defined along the length of the body, each of the plurality of longitudinal flutes having increasing width from the proximal end to the distal end of the body, wherein the body is made from a carbon material.

In a further embodiment of the drainage device, a thoracic catheter may include a body having a round cross-section defining a plurality of lumens in communication with multiple longitudinal flutes defined along the entire length of the body, the body further including a terminal point that is substantially perpendicular to the body and in communication with the plurality of lumens, wherein the body is made from a carbon material.

In one other embodiment of the drainage device, a central venous access device may include a body having a plurality of lumens and formed with a plurality of longitudinal flutes, the body defining a proximal opening and a distal opening in communication with the plurality of lumens, wherein the body is made from a carbon material.

Various preferred embodiments of any of the drainage devices may comprise carbon-based structures having a plurality of carbon nanotubes. The carbon nanotubes may be functionalized or attached to a base structure such as carbon fibers or carbon paper. The carbon-based structure may comprise a composite of a plurality of carbon nanotubes attached to carbon fibers and then impregnated with a physiologically inert material. Additional preferred embodiments of any of the drainage devices may comprise carbon materials specially chosen and fabricated to be effectively elastomeric in nature and also to suppress FGF2 to inhibit growth of fibroblasts.

These and other features, aspects, and advantages of the present invention will become better understood with reference to the following description, appended claims, and accompanying drawings.

BRIEF DESCRIPTION OF THE DRAWINGS

Though the specification concludes with claims particularly pointing out and distinctly claiming the invention, it is believed that the present invention will be better understood from the following description taken in conjunction with the accompanying drawings, in which:

Corresponding reference characters indicate corresponding elements among the view of the drawings. The headings used in the figures should not be interpreted to limit the scope of the claims.

DETAILED DESCRIPTION

Features and advantages of the invention will now be described with occasional reference to specific embodiments. However, the invention may be embodied in different forms and should not be construed as limited to the embodiments set forth herein. Rather, these embodiments are provided so that this disclosure will be thorough and complete and will fully convey the scope of the invention to those skilled in the art.

Unless otherwise defined, all technical and scientific terms used herein have the same meaning as commonly understood by one of ordinary skill in the art to which the invention belongs. The terminology used in the description herein is for describing particular embodiments only and is not intended to be limiting. As used in the specification and appended claims, the singular forms "a," "an," and "the" are intended to include the plural forms as well, unless the context clearly indicates otherwise.

Figure 1:
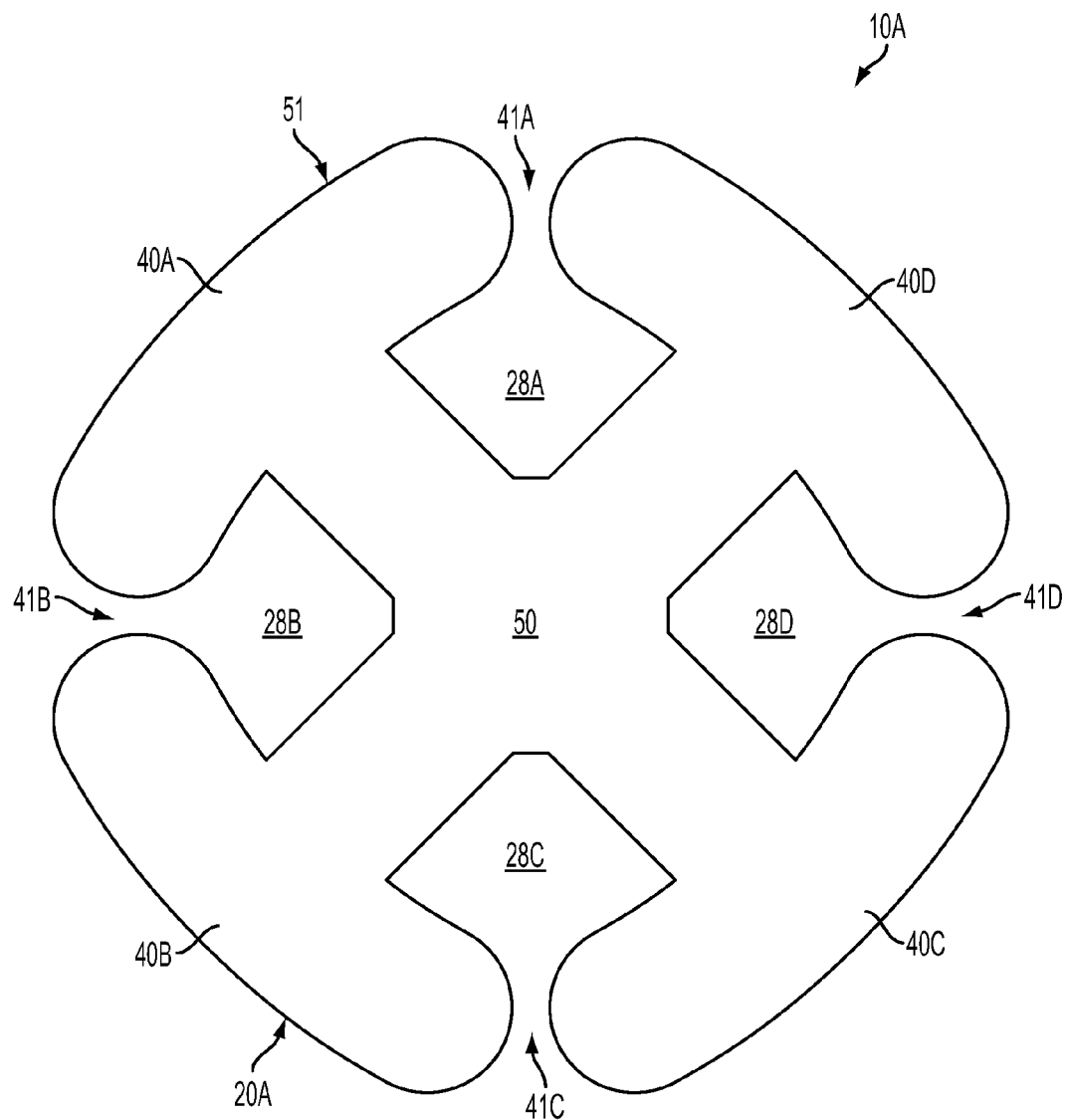
FIG. 1 is a cross-sectional view of an embodiment of an ophthalmic shunt.
Figure 82:
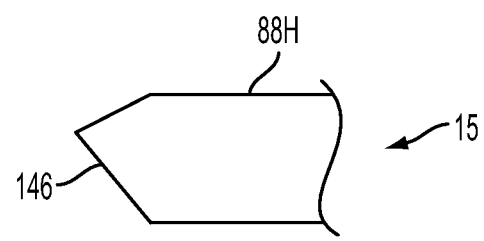
FIG. 82 is a side view of a central venous access device showing an end point with an asymmetrical configuration.

Referring to the drawings, embodiments for various drainage devices, particularly ophthalmic shunts, hydrocephalus shunts, artificial meshes, arteriovenous shunts, thoracic catheters, and central venous access devices, are illustrated and generally indicated as 10, 11, 12, 13, 14 and 15, respectively, in FIGS. 1-82. As used herein, the term "drainage device" refers to any type of drainage device used in the medical arts to drain fluids from the body. Though "drainage device" encompasses ophthalmic shunts, hydrocephalus shunts, artificial meshes, arteriovenous shunts, thoracic catheters, and central venous access devices, it will be understood that these are intended as non-limiting examples of drainage devices.

It is believed that materials comprising various forms of carbon or carbon-based materials may exhibit substantial anti-angiogenic activity against the human growth factor FGF2. Suppression of FGF2 may inhibit proliferative growth of fibroblasts. Therefore, preferred embodiments of various drainage devices described herein may comprise one or more components comprising, consisting essentially of, or consisting of a form of pure carbon, at least one carbon-based structure, a composite comprising pure carbon or at least one carbon-based structure, or combinations of these. As used herein, the terms "form of pure carbon" and "carbon-based material" refer to the common allotropic forms of carbon (for example, amorphous carbon, carbon black, and graphite) and to any material consisting essentially of a network of covalently bonded carbon atoms. Examples of materials consisting essentially of a network of covalently bonded carbon atoms include, but are not limited to, carbon fibers, carbon nanotubes, functionalized carbon nanotubes, carbon nanoparticles, and buckyballs. As used herein, the term "carbon-based structure" encompasses structures made by physically or chemically connecting one or more forms of pure carbon, defined as above. As a non-limiting example, growth of carbon nanotubes on carbon fibers produces one type of carbon-based structure. Carbon materials and composites of carbon materials in general are known for their inherent rigidity. Therefore, further preferred embodiments of various drainage devices described herein may comprise carbon materials specially chosen and fabricated to be effectively elastomeric in nature and also to suppress FGF2 to inhibit growth of fibroblasts.

Several embodiments described below relate to drainage devices for glaucoma, particularly to ophthalmic shunts. The ophthalmic shunts may include a proximal catheter suitable to be extended into the anterior chamber of the eye. In many embodiments, the proximal catheter may be fabricated from a material comprising pure carbon, a carbon-based structure, or both, and be constructed in such a manner that multiple pathways for egress exist.

The pathways may consist of grooves within the surface of the catheter, extruded into the catheter at the time of fabrication, and may run substantially longitudinally from the proximal tip of the catheter to its termination point. The pathways may rely upon capillary action for their functioning, as they are configured to drain fluid from a pressurized environment (the anterior chamber) to an environment of normal ambient pressure, such as the subconjunctival space, the suprachoroidal space, or some alternate area of the eye. The catheter may terminate either at one of these specified anatomical points or, alternatively, may be connected to a valved reservoir assembly.

The valved reservoir may allow for the maintenance of intraocular pressure within a desired range and may permit the accumulation of drained fluid within the reservoir for sampling, injection, or both. In many embodiments, the valved reservoir assembly may be constructed from the same or similar carbon and/or carbon based elastomeric materials to inhibit fibroblast growth. In preferred embodiments, the drainage device maintains the desired qualities of conformability and pliability so as to minimize tissue erosion and disruption of the implant during routine ocular motility.

FIGS. 1-19 illustrate specific example embodiments for an ophthalmic shunt 10 used to shunt fluid from the anterior chamber of a patient's eye to another site within the eye having a lower ambient pressure. By operation of the ophthalmic shunt 10, fluid essentially may be forced from the anterior chamber of the eye. The ophthalmic shunt 10 may be made entirely of a carbon material, and in other embodiments the ophthalmic shunt 10 may be made from some form of carbon in combination with another physiologically inert material, such as gold, silver, PMMA, or niobium.

Referring to FIG. 1, one embodiment of the ophthalmic shunt 10A may include a body 20A having a plurality of flutes 40A-D that meet at a central stem 50 with a respective slit 41A-D defined between each flute 40. As shown, each slit 41A-D communicates directly with a respective conduit 28A-D adapted for fluid flow communication therethrough.

Figure 2:
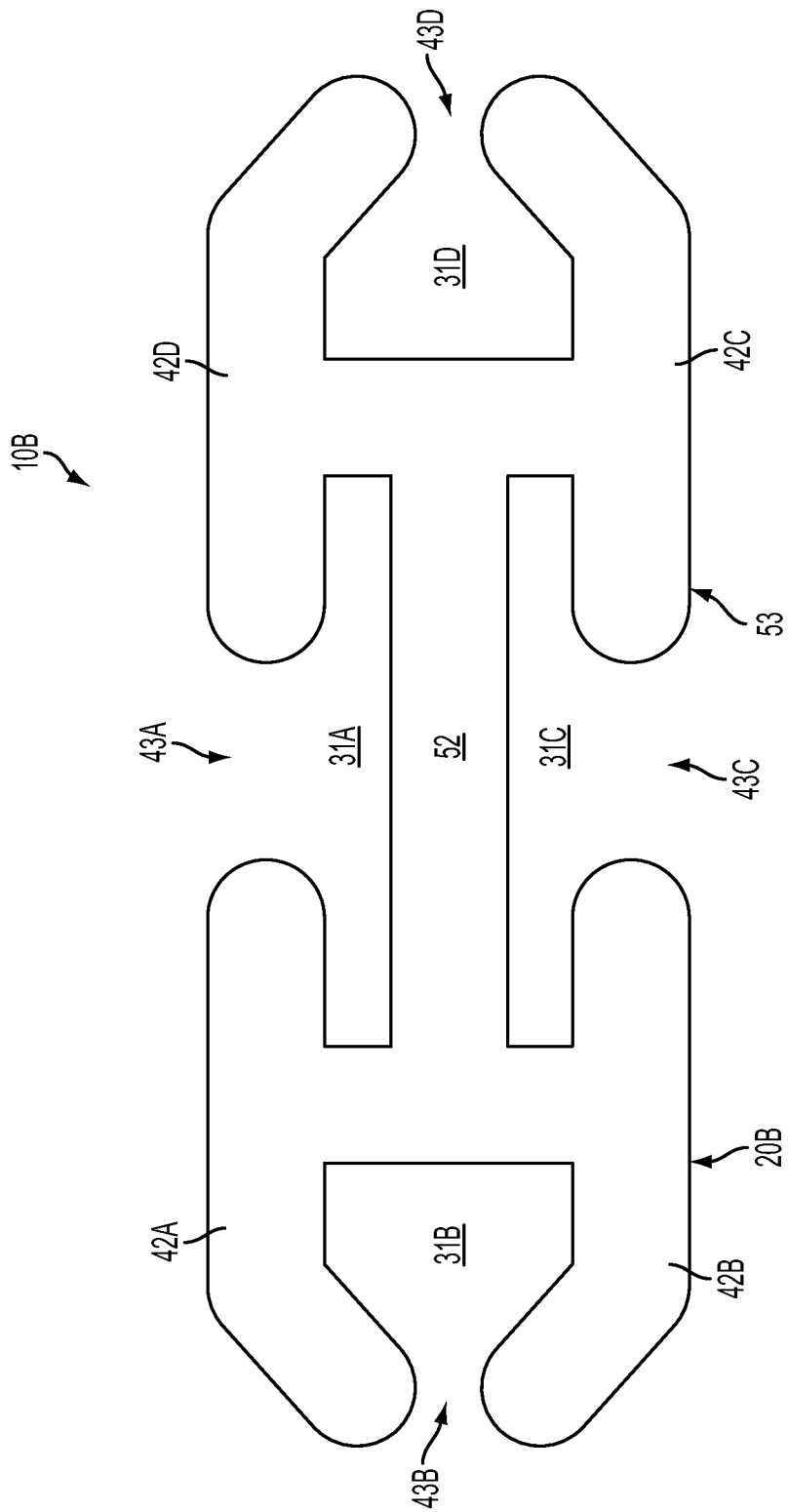
FIG. 2 is a cross-sectional view of another embodiment of the ophthalmic shunt with varied sized openings between the flutes.
Figure 3:
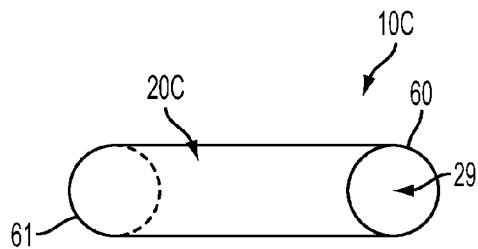
FIG. 3 is a side view of yet another embodiment of the ophthalmic shunt having a carbon tube defining a single conduit.
Figure 4:
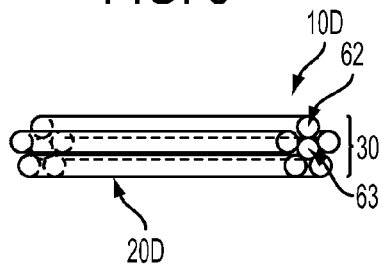
FIG. 4 is a side view of one embodiment of the ophthalmic shunt having multiple carbon tubes defining multiple conduits.
Figure 5:
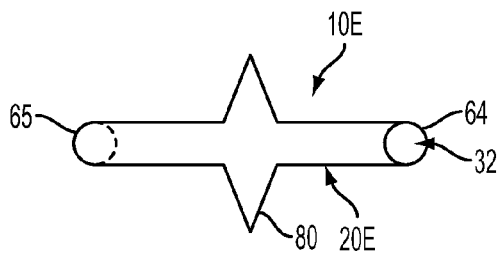
FIG. 5 is a side view of a further embodiment of the ophthalmic shunt having a carbon tube with a single collar.

As shown in FIG. 2, another embodiment of the ophthalmic shunt 10B may include a body 20B having a plurality of flutes 42A-D that meet at a central stem 52 with a respective slit 43A-D defined between each flute 42. In this embodiment, slits 43A and 43C may have a differently sized opening with respect to slits 43B and 43D. Each slit 43A-D is in communication with a respective conduit 31A-D with conduits 31A and 31C having a different configuration with respect to conduits 31B and 31D. Similar to ophthalmic shunt 10A, conduits 31A-D of ophthalmic shunt 10B are adapted for fluid flow communication for shunting fluid.

Figure 7:
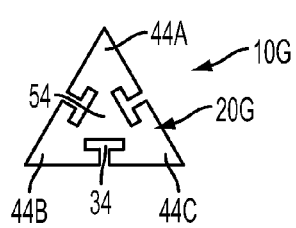
FIG. 7 is a cross-sectional view of an embodiment of the ophthalmic shunt having a triangular-shaped configuration.
Figure 8:
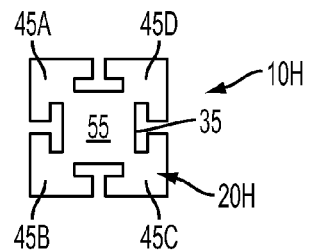
FIG. 8 is a cross-sectional view of an embodiment of the ophthalmic shunt having a square-shaped configuration.
Figure 9:
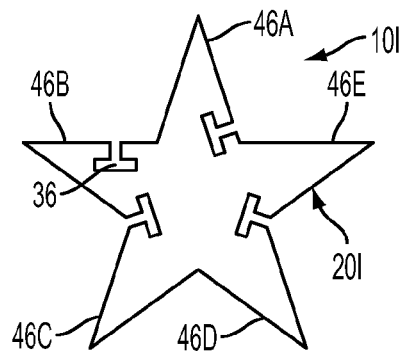
FIG. 9 is a cross-sectional view of an embodiment of the ophthalmic shunt having a star-shaped configuration.

Referring to FIGS. 7-9, various embodiments of the ophthalmic shunt 10 having flutes with various configurations are illustrated. As shown in FIG. 7, ophthalmic shunt 10G has a triangular configuration and includes three flutes 44A, 44B and 44C that meet at a stem 54 and define three separate conduits 34, while ophthalmic shunt 10H has a square or rectangular configuration and includes four flutes 45A, 45B, 45C and 45D that meet at stem 55 and define four separate conduits 35. In addition, an embodiment of the ophthalmic shunt 10I has a star-shaped configuration and includes five flutes 46A, 46B, 46C, 46D and 46E that define four separate conduits 36.

Figure 6:
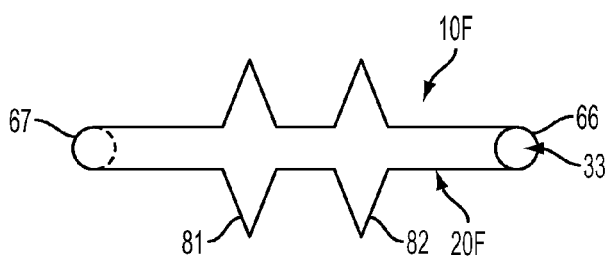
FIG. 6 is side view of another embodiment of the ophthalmic shunt having a carbon tube with a dual collar.

Referring to FIGS. 3-6, various tubular embodiments of the ophthalmic shunt 10 are shown. The ophthalmic shunt 10C shown in FIG. 3 includes a tubular body 20C having a conduit 29 that communicates with a distal opening 60 and an opposing proximal opening 61 adapted to shunt fluid therethrough, while the ophthalmic shunt 10D shown in FIG. 4 includes multiple tubular body 20D having multiple conduits 30 that communicate with a distal opening 62 and an opposing proximal opening 63 adapted to shunt fluid through each respective one of the multiple conduits 30. In addition, the ophthalmic shunt 10E shown in FIG. 5 includes a tubular body 20E that defines a conduit 32 that communicates with a distal opening 64 and an opposing proximal opening 65 with a collar 80 defined along the tubular body 20E as a means for engaging the ophthalmic shunt 10E to a patient's structural body part. Referring to FIG. 6, the ophthalmic shunt 10F includes a tubular body 20F having a single conduit 33 in communication with a distal opening 66 and an opposing proximal opening 67 with a pair of collars 81, 82 defined along the tubular body 20F adapted to engage the ophthalmic shunt 10F to the patient's structural body part.

Figure 10:
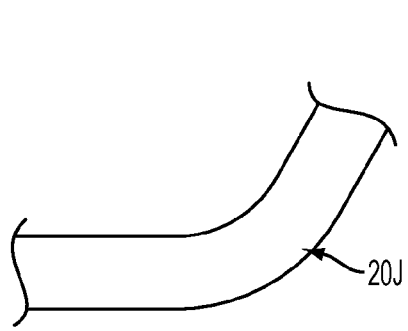
FIG. 10 is a partial side view of one embodiment of the ophthalmic shunt having a curved configuration.
Figure 11:
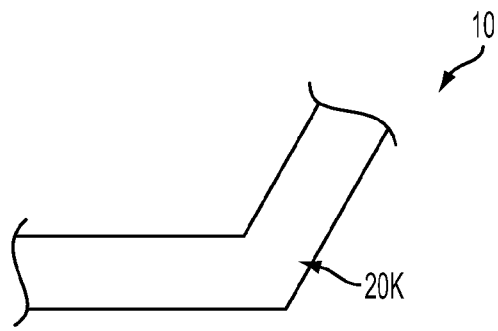
FIG. 11 is a side view of one embodiment of the ophthalmic shunt having an angled configuration.

As shown in FIGS. 10 and 11, any of the tubular embodiments of ophthalmic shunts 10C, 10D, 10E and 10F may have various configurations. For example, ophthalmic shunt 10 may include a curved body 20J that has a curved configuration, while another ophthalmic shunt 10 may include an angled body 20K having an angled configuration. As such, the ophthalmic shunts 10C, 10D, 10E and 10F may have either curved or angled configurations for the tubular body of the ophthalmic shunt 10.

Figure 12:
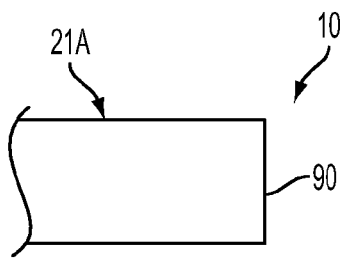
FIG. 12 is an enlarged side view of one embodiment of the ophthalmic shunt showing an end point with a flush configuration.
Figure 13:
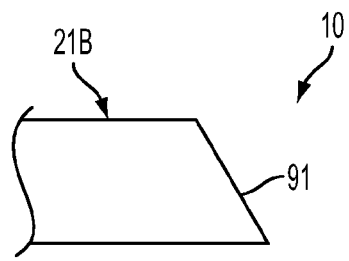
FIG. 13 is an enlarged side view of one embodiment of the ophthalmic shunt showing an end point with an angled configuration.
Figure 14:
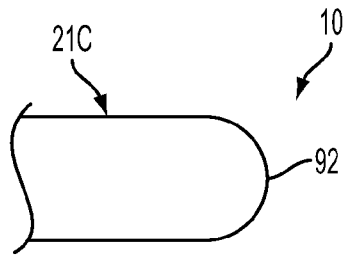
FIG. 14 is an enlarged side view of one embodiment of the ophthalmic shunt showing an end point with a curved configuration.
Figure 15:
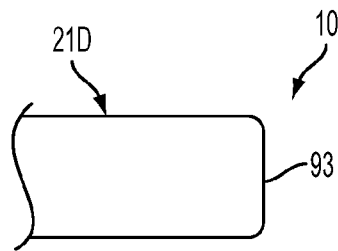
FIG. 15 is an enlarged side view of one embodiment of the ophthalmic shunt showing an end point with rounded edges.
Figure 16:
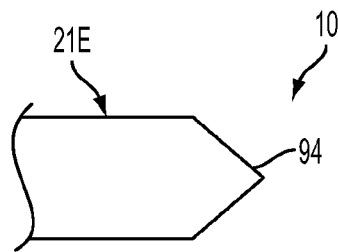
FIG. 16 is an enlarged side view of one embodiment of the ophthalmic shunt showing an end point with a pointed configuration.
Figure 17:
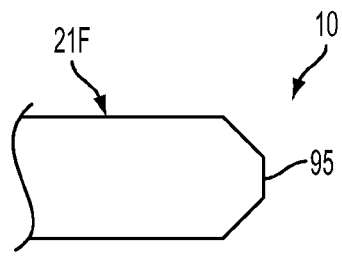
FIG. 17 is an enlarged side view of one embodiment of the ophthalmic shunt showing an end point with a trapezoidal configuration.
Figure 18:
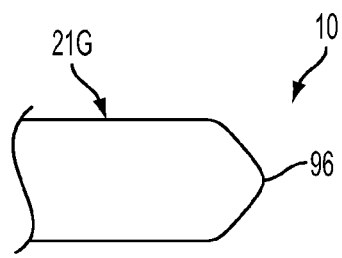
FIG. 18 is an enlarged side view of one embodiment of the ophthalmic shunt showing an end point with a dome-shaped configuration.
Figure 19:
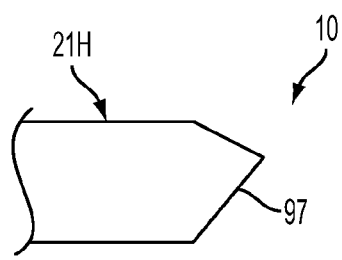
FIG. 19 is an enlarged side view of one embodiment of the ophthalmic shunt showing an end point with an asymmetrical pointed configuration.

Referring to FIGS. 12-18, any of the embodiments of the ophthalmic shunt 10 discussed above may have end points 21 with various configurations. For example, as shown in FIG. 12, ophthalmic shunt 10 may have an end point 21A defining a flush edge 90, while another embodiment of ophthalmic shunt 10 may have an end point 21B defining an angled edge 91 as shown in FIG. 13. In addition, the ophthalmic shunt 10 may include an end point 21C (FIG. 14) having a curved edge 92 that may represent as much as a 180° arc in one embodiment. With respect to other embodiments of the ophthalmic shunt 10, end point 21D may define a rectangular-shaped rounded edge 93 (FIG. 15) to minimize trauma during placement and retention of the ophthalmic shunt 10 into the patient's eye, end point 21E may define a pointed edge 94 (FIG. 16), end point 21F may define a trapezoidal-shaped edge 95 (FIG. 17), end point 21G may define a dome-shaped edge 96 (FIG. 18), and end point 21H may define an asymmetrically pointed edge 97 (FIG. 19) that results in the smooth passage and self-dilating effect of the ophthalmic shunt 10 as the ophthalmic shunt 10 passes through the patient's tissue.

In another aspect of ophthalmic shunt 10, the shunts discussed above may be fabricated using different materials and manufacturing techniques. In one embodiment, the ophthalmic shunt 10 may be fabricated exclusively from pure carbon; however, other fabrication techniques are contemplated for manufacturing other embodiments of the ophthalmic shunt 10 using a substrate. For example, the ophthalmic shunt 10 may be fabricated from a graphite substrate, metal substrate, any electrically conductive substrate, PMMA substrate, polymer substrate, or ceramic substrate with vapor deposition of pure carbon to these substrates being applied in an intimately conformal manner. In another embodiment, the ophthalmic shunt 10 may be made from a composite of polymer and carbon with the polymer being substantially infused with the carbon particles, while in another embodiment the ophthalmic shunt 10 may be made from a composite of elastomer and carbon with the elastomer being substantially infused with carbon particles.

In yet another aspect of the ophthalmic shunt 10, the shunts discussed above may be fabricated using electrical discharge machining and/or subsequent vapor deposition of carbon, injection molding and/or subsequent vapor deposition of carbon. Other fabrication techniques may include stamping and/or subsequent vapor deposition of carbon as well as extrusion and subsequent vapor deposition of carbon.

In preferred embodiments of the ophthalmic shunt 10, any of the shunts discussed above may be fabricated from materials comprising pure carbon or at least one carbon-based material such as a carbon fiber, carbon nanotubes, carbon preforms, or buckyballs. In especially preferred embodiments, the shunts may comprise functionalized carbon nanotubes. As used herein, the term "functionalized carbon nanotubes" refers to carbon nanotubes having one or both ends chemically attached to at least one base material. As such, a structure including functionalized carbon nanotubes would necessarily include at least one base material and a plurality carbon nanotubes attached to the at least one base material. Though in some preferred embodiments the ophthalmic shunt 10 may be made exclusively of the materials comprising pure carbon or at least one carbon-based structure, in other preferred example embodiments, the materials may be present as fibroblast-inhibiting layers on inner walls of the conduit in communication with the fluid flowing through the conduit. The fibroblast-inhibiting layers may be attached to the inner walls and may intimately conform to the contours of the inner walls, such that fibroblast growth will be inhibited along the entire flow path of the conduit. The materials described with respect to these preferred embodiments may exhibit not only the flexibility desirable for drainage devices, but also a substantial anti-angiogenic activity against FGF2.

In one specific example, the base material may comprise a thin carbon scaffold consisting essentially of carbon fibers. Suitable carbon scaffolds in this regard include, for example, carbon veils, carbon-fiber tissues, and carbon-fiber mats. Though the carbon scaffold may be used alone, carbon nanotubes many be grown on the carbon scaffold to form in a fuzzy veil of carbon fibers. The term "fuzzy veil" refers to the ragged appearance of the original veil, tissue, or mat of carbon fibers under a microscope after nanotubes are grown on the carbon fibers. In still further examples, the fuzzy veil may be coated, for example by impregnation or other suitable technique, with a flexible and conformal polymer such as, for example, polymethylmethacrylate, to form a flexible composite.

In still further examples, the base material may comprise a two-dimensional carbon preform consisting essentially of a plurality of carbon-fiber tows. Likewise, carbon nanotubes may be grown on the carbon preform and optionally coated with a flexible polymeric material. In still further examples, the base material may comprise a carbon paper consisting essentially of carbon nanotubes and carbon nanofibers, prepared using a slurry technique analogous to slurry techniques commonly used in the art of cellulose paper manufacturing.

Figure 20:
FIG. 20 is a side view of a hydrocephalus shunt having an elongated single conduit configuration.
Figure 21:
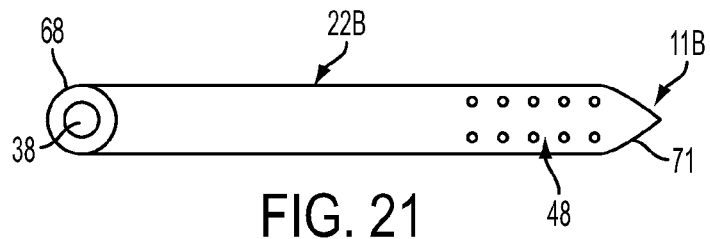
FIG. 21 is a side view of a hydrocephalus shunt having a shortened single conduit configuration.

Referring to FIGS. 20-26, different embodiments of the hydrocephalus shunt 11 having various structural configurations will be discussed. The hydrocephalus shunt 11 is used to shunt fluid from the lateral ventricles of the brain to either the peritoneum or the atrium of the heart. As shown in FIG. 20, an embodiment of the hydrocephalus shunt 11A, includes a generally shortened tubular body 22A that defines a single conduit 37 adapted for shunting fluid and a distal end portion 70 having a plurality of openings 47 in fluid flow communication with the conduit 37 for shunting fluid through the hydrocephalus shunt 11A. In another embodiment of the hydrocephalus shunt 11B, as illustrated in FIG. 21, the hydrocephalus shunt 11B includes a generally lengthened tubular body 22B defining a proximal opening 68 and a distal portion 71 with the proximal opening 68 being in communication with a single conduit 38. In addition, the proximal portion 71 of the hydrocephalus shunt 11B is in communication with a plurality of openings 48 that are in fluid flow communication with the single conduit 38 for shunting fluid.

Figure 22:
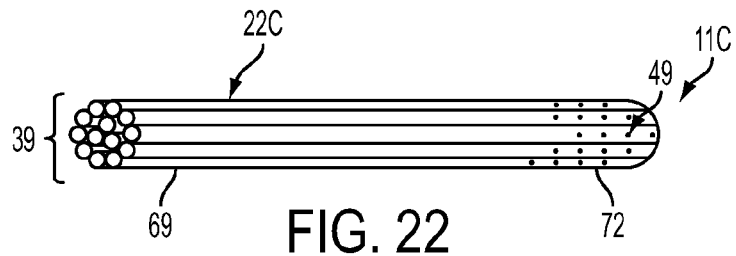
FIG. 22 is a side view of a hydrocephalus shunt having a multiple conduit configuration.
Figure 23:
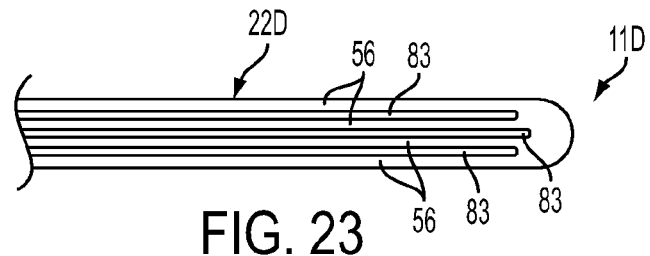
FIG. 23 is a side view of a hydrocephalus shunt having a multiple flute configuration defining multiple openings.
Figure 24:
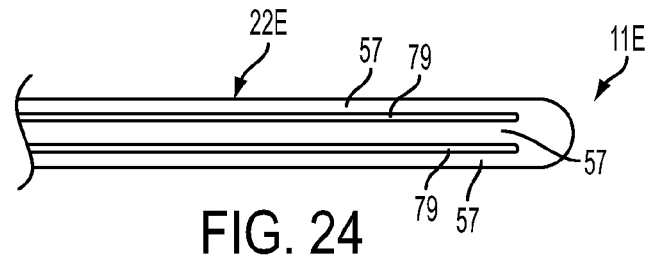
FIG. 24 is a side view of a hydrocephalus shunt having a multiple flute configuration defining multiple gradually widening openings.

In yet another embodiment of the hydrocephalus shunt 11C, illustrated in FIG. 22, the hydrocephalus shunt 11C includes a generally tubular body 22C defining a proximal portion 69 and a distal portion 72 with the proximal portion 69 in communication with a plurality of conduits 39. The distal portion 72 includes a plurality of openings 49 in communication with the plurality of conduits 39 for shunting fluid through the hydrocephalus shunt 11C. One embodiment of the hydrocephalus shunt 11D, is shown in FIG. 23 and includes a body 22D that defines a plurality of flutes 56 interposed between a respective number of slits 83 that communicate with one or more conduits (not shown) for shunting fluid through the hydrocephalus shunt 11D. Another embodiment of the hydrocephalus shunt 11E is shown in FIG. 24 and also includes a body 22E that defines a plurality of flutes 57 interposed between a respective number of increasingly widening slits 79 that communicate with one or more internal conduits (not shown) for shunting fluid through hydrocephalus shunt 11E. In one embodiment, the hydrocephalus shunt 11 may be fabricated from a carbon infused elastomer using either injection molding or an extrusion process known in the art.

Figure 25:
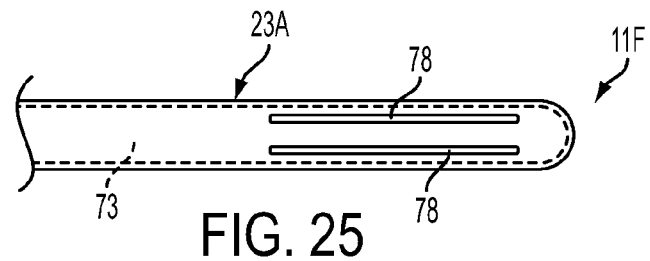
FIG. 25 is a side view of a distal catheter for a hydrocephalus shunt having multiple slits that communicate with a single conduit.
Figure 26:
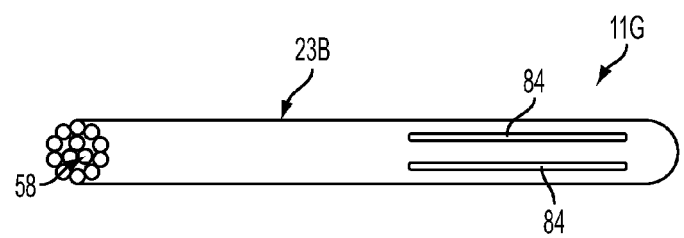
FIG. 26 is a side view of a distal catheter for a hydrocephalus shunt having a multiple slits that communicate with multiple conduits.
Figure 27A:
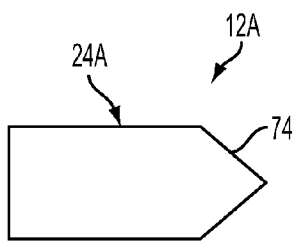
FIG. 27A is a top view of an artificial mesh made from a single carbon sheet having a pointed end configuration.
Figure 27B:
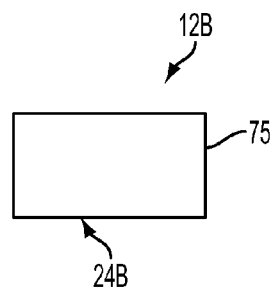
FIG. 27B is a top view of an artificial mesh made from a single carbon sheet having a rectangular configuration.
Figure 27C:
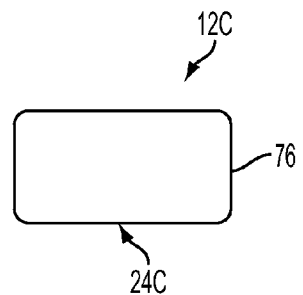
FIG. 27C is a top view of an artificial mesh made from a single carbon sheet having a rectangular configuration with rounded edges.

In another aspect of the hydrocephalus shunt 11 shown in FIG. 25, a proximal catheter 11F is in fluid flow communication with the hydrocephalus shunt 11 and is disposed in the brain to draw fluid from that area of the brain through the proximal catheter 11F and hydrocephalus shunt 11. As shown, the proximal catheter 11F may include a catheter body 23A defining a single conduit 73 (shown in phantom) in communication with a plurality of shortened slits 78 for shunting fluid through the proximal catheter 11F. Referring to FIG. 26, in another embodiment the proximal catheter 11G may include a catheter body 23B that defines a plurality of shortened slits 84 in communication with a plurality of conduits 58 adapted for shunting fluid through the hydrocephalus shunt 11.

In preferred embodiments of the hydrocephalus shunt 11, any of the shunts discussed above may be fabricated from materials comprising pure carbon or at least one carbon-based material such as a carbon fiber, carbon nanotubes, carbon preforms, or buckyballs. In especially preferred embodiments, the shunts may comprise functionalized carbon nanotubes. As used herein, the term "functionalized carbon nanotubes" refers to carbon nanotubes having one or both ends chemically attached to at least one base material. As such, a structure including functionalized carbon nanotubes would necessarily include at least one base material and a plurality carbon nanotubes attached to the at least one base material. In any respect, the carbon or carbon-based material is configured to inhibit growth of fibroblasts in the conduit. As used herein, "configured to inhibit growth of fibroblasts in the conduit" means that at least the surfaces of the body defining the inner walls of the conduit are made from or are covered with the carbon or carbon-based material. Though in some preferred embodiments the hydrocephalus shunt 11 may be made exclusively of the materials comprising pure carbon or at least one carbon-based structure, in other preferred example embodiments, the materials may be present as fibroblast-inhibiting layers on inner walls of the conduit in communication with the fluid flowing through the conduit. The fibroblast-inhibiting layers may be attached to the inner walls and may intimately conform to the contours of the inner walls, such that fibroblast growth will be inhibited along the entire flow path of the conduit. The materials described with respect to these preferred embodiments may exhibit not only the flexibility desirable for drainage devices, but also a substantial anti-angiogenic activity against FGF2.

In one specific example, the base material may comprise a thin carbon scaffold consisting essentially of carbon fibers. Suitable carbon scaffolds in this regard include, for example, carbon veils, carbon-fiber tissues, and carbon-fiber mats. Though the carbon scaffold may be used alone, carbon nanotubes many be grown on the carbon scaffold to form in a fuzzy veil of carbon fibers. The term "fuzzy veil" refers to the ragged appearance of the original veil, tissue, or mat of carbon fibers under a microscope after nanotubes are grown on the carbon fibers. In still further examples, the fuzzy veil may be coated, for example by impregnation or other suitable technique, with a flexible and conformal polymer such as, for example, polymethylmethacrylate, to form a flexible composite.

In still further examples, the base material may comprise a two-dimensional carbon preform consisting essentially of a plurality of carbon-fiber tows. Likewise, carbon nanotubes may be grown on the carbon preform and optionally coated with a flexible polymeric material. In still further examples, the base material may comprise a carbon paper consisting essentially of carbon nanotubes and carbon nanofibers, prepared using a slurry technique analogous to slurry techniques commonly used in the art of cellulose paper manufacturing.

Referring to FIGS. 27-30, various embodiments of the artificial mesh 12 will be discussed in greater detail. The artificial mesh 12 may be used in glaucoma surgery where the paramount concern is to create and maintain a patent fistula for the drainage of fluid from the anterior chamber of the eye. For example, in a trabeculotomy or a trabeculectomy, a piece of tissue from the trabecular meshwork is removed from the point in the eye where the iris meets the sclera to drain intraocular fluid. During such surgical procedures, Mitomycin-c and other anti-metabolites may be used to assist in maintaining the patency of the trabeculotomy, by either selective or non-selective FGF-2 and/or VEGF. As such, the artificial mesh 12 with a thin layer of carbon mesh over the trabeculotomy beneath the surgical flap has been found to maintain the patency of the trabeculotomy. In an embodiment of the artificial mesh 12A, illustrated in FIG. 27A, the artificial mesh 12A includes an artificial mesh body 24A that may be fabricated from a single sheet of carbon having a pointed side 74. In one embodiment of the artificial mesh 12B, as shown in FIG. 27B, may also be fabricated from a single sheet of carbon including an artificial mesh body 24B having rectangular-shaped configuration, while another embodiment of the artificial mesh 12C, illustrated in FIG. 27C, may be made from the same carbon material and include an artificial mesh body 24C having a generally rectangular shape but defining rounded edges.

Figure 28:
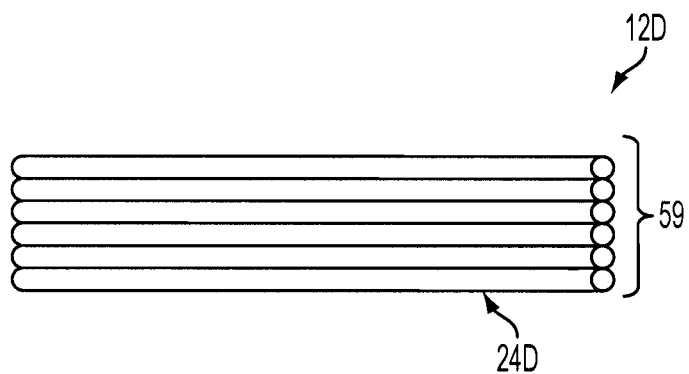
FIG. 28 is a top view of an artificial mesh made from a longitudinal arrangement of multiple carbon nanotubes.
Figure 29:
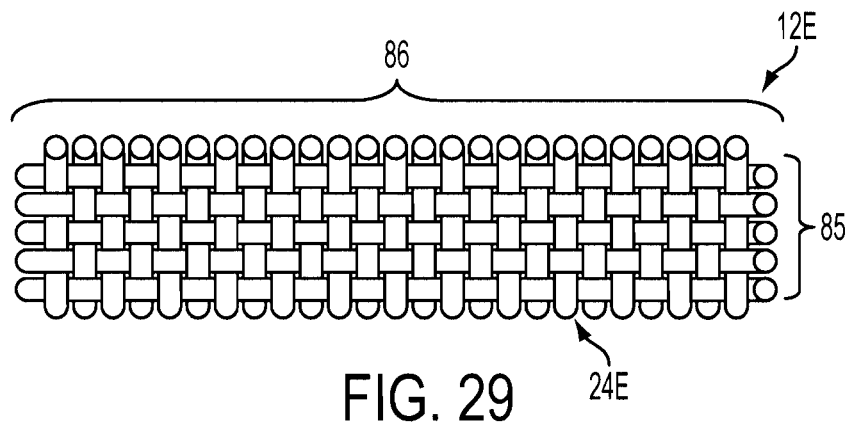
FIG. 29 is a top view of an artificial mesh made from a vertical and horizontal oriented multiple carbon nanotubes.
Figure 30:
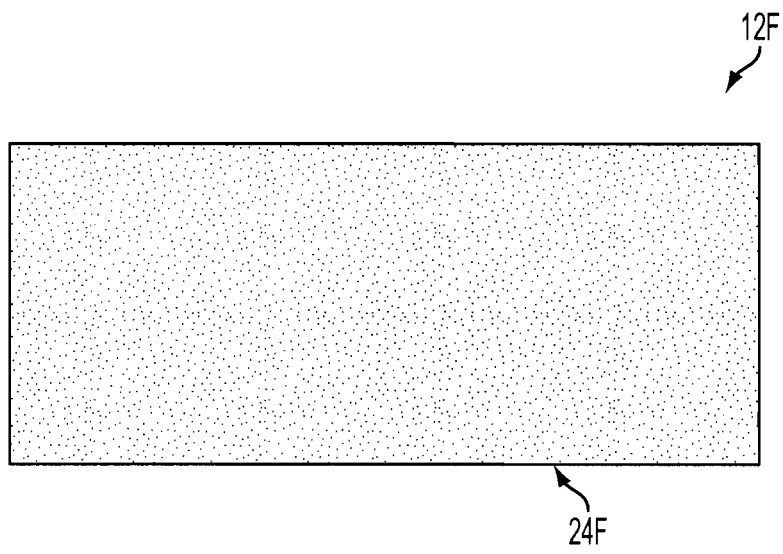
FIG. 30 is a top view of an artificial mesh made from an elastomer formed with carbon particles.

Other embodiments of the artificial mesh are also contemplated. As shown in FIG. 28, an embodiment of the artificial mesh 12D includes an artificial mesh body 24D having a plurality of longitudinally arranged nanotubes 59. Referring to FIG. 29, another embodiment of the artificial mesh 12E includes an artificial mesh body 24E having a plurality of horizontally aligned nanotubes 85 in weaved layers with vertically aligned nanotubes 86. Another embodiment of the artificial mesh 12F may include an artificial mesh body 24F made from an elastomer impregnated with carbon particles or nanotubes.

The artificial mesh 12 may be fabricated using various manufacturing materials. In one aspect, the artificial mesh 12 may be fabricated from a sheet of elastomer material, acting as a substrate, that is impregnated with carbon particles or carbon nanotubes. In another process of fabrication, a sheet of elastomer material may have a surface treatment of at least one sheet of carbon nanotubes or a layer of vapor deposited carbon. Other substrate materials used for fabrication may be made from a metal-based substance, including but not limited to gold, silver, nickel, and/or titanium. In addition, the substrate may be made from a polymer-based substance, such as a polymer substrate infused with carbon particles or carbon nanotubes, a polymer substrate coated with vapor deposited carbon particles, or a polymer substrate fixed with a surface treatment of at least one layer of nanotubes.

The artificial mesh 12 may also be fabricated from other substrate materials. In one embodiment, a metal substrate may be coated with vapor-deposited carbon particles. The metal substrate may also be infused with carbon particles or carbon nanotubes, or fixed with a surface treatment of at least one layer of carbon nanotubes. In another embodiment, the artificial mesh 12 may be made from a carbon substrate that is plated, in whole or in part, with a metal substance, including but not limited to gold, silver, and/or nickel. In the alternative, the artificial mesh 12 may be made from a carbon substrate that is coated by vapor deposition, either in whole or in part, with a metal substance, including but not limited to gold, silver, titanium, tantalum, and/or niobium.

In preferred embodiments of the artificial mesh 12, any of the substrate materials discussed above may comprise pure carbon or at least one carbon-based material such as a carbon fiber, carbon nanotubes, carbon preforms, or buckyballs. In especially preferred embodiments, the substrate material may comprise functionalized carbon nanotubes. In further preferred embodiments, the body of the artificial mesh 12 comprises a plurality of carbon nanotubes, such that the individual carbon nanotubes each define a conduit through the inside of the individual carbon nanotubes. As such, the carbon-based structure configured to inhibit growth of fibroblasts in the conduct comprises all of the individual carbon nanotubes that function as separate conduits for the flow of fluid.

In one specific example, the base material may comprise a thin carbon scaffold consisting essentially of carbon fibers.

Suitable carbon scaffolds in this regard include, for example, carbon veils, carbon-fiber tissues, and carbon-fiber mats. Though the carbon scaffold may be used alone, carbon nanotubes many be grown on the carbon scaffold to form in a fuzzy veil of carbon fibers. The term "fuzzy veil" refers to the ragged appearance of the original veil, tissue, or mat of carbon fibers under a microscope after nanotubes are grown on the carbon fibers. In still further examples, the fuzzy veil may be coated, for example by impregnation or other suitable technique, with a flexible and conformal polymer such as, for example, polymethylmethacrylate, to form a flexible composite.

In still further examples, the base material may comprise a two-dimensional carbon preform consisting essentially of a plurality of carbon-fiber tows. Likewise, carbon nanotubes may be grown on the carbon preform and optionally coated with a flexible polymeric material. In still further examples, the base material may comprise a carbon paper consisting essentially of carbon nanotubes and carbon nanofibers, prepared using a slurry technique analogous to slurry techniques commonly used in the art of cellulose paper manufacturing.

Referring to FIGS. 31-48, various embodiments of the arteriovenous shunt 13 are described. The arteriovenous shunt 13 may be implanted into kidney-dialysis patients to allow easy and repeated access to the patient's bloodstream. As a matter of routine, prior art arteriovenous shunts can become clogged, thereby requiring regular flushing and ultimate replacement of such shunts. In one aspect, the arteriovenous shunt 13 may be fabricated from a carbon-based structure such that the arteriovenous shunt 13 would either substantially inhibit or prevent clogging.

Figure 31:
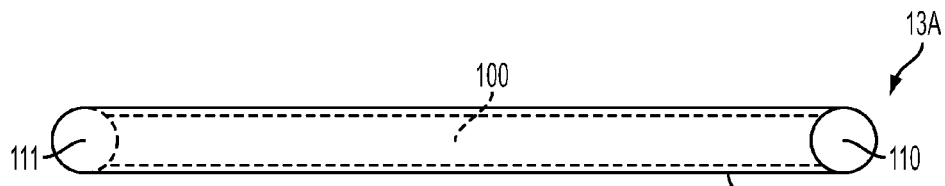
FIG. 31 is a side view of one embodiment of an arteriovenous shunt having a single lumen.
Figure 32:
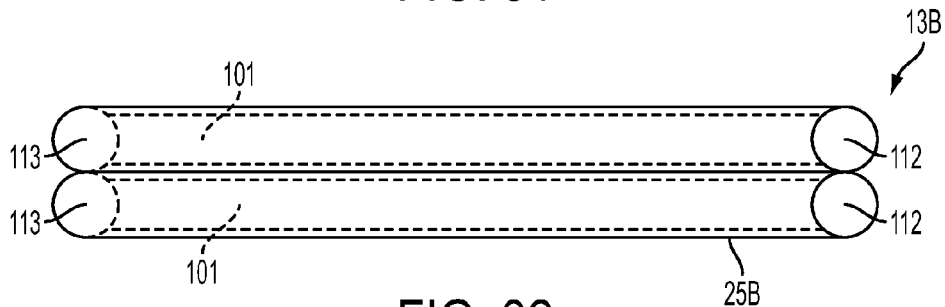
FIG. 32 is a side view of another embodiment of the arteriovenous shunt having multiple lumens.
Figure 33:
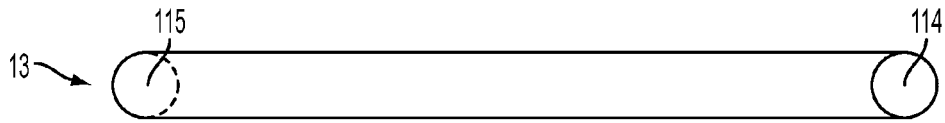
FIG. 33 is a side view of one embodiment of the arteriovenous shunt having oval-shaped openings.
Figure 34:
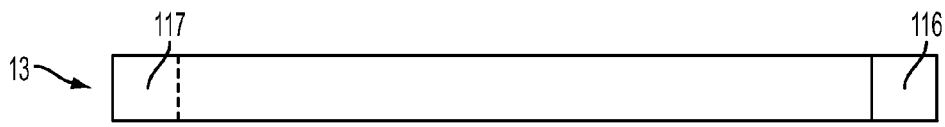
FIG. 34 is a side view of one embodiment of the arteriovenous shunt having square-shaped openings.
Figure 35:
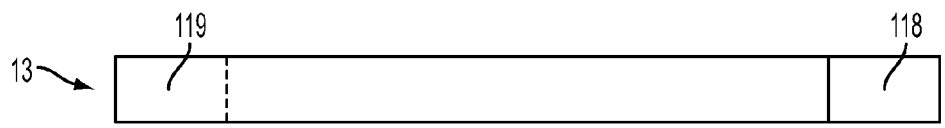
FIG. 35 is a side view of one embodiment of the arteriovenous shunt having rectangular-shaped openings.
Figure 36:
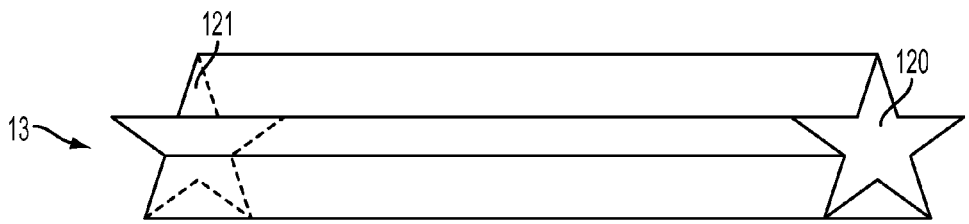
FIG. 36 is a side view of one embodiment of the arteriovenous shunt having star-shaped openings.

The embodiment of the arteriovenous shunt 13A shown in FIG. 31 includes a tubular-shaped arteriovenous shunt body 25A defining opposing circular distal and proximal openings 110 and 111 that communicate with a conduit 100 (shown in phantom) adapted to shunt fluid therethrough, while the arteriovenous shunt 13B shown in FIG. 32 includes a multiple tubular-shaped arteriovenous shunt body 25B defining a plurality of conduits 101 that communicate with respective opposing circular distal and proximal openings 112 and 113.

Figure 37:
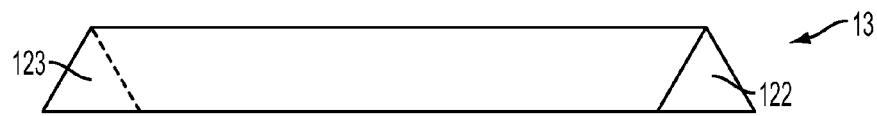
FIG. 37 is a side view of one embodiment of the arteriovenous shunt having triangular-shaped openings.

Referring to FIGS. 33-37, any of the tubular embodiments of arteriovenous shunt 13 may have openings with different cross-sectional configurations. For example, arteriovenous shunt 13 may define opposing oval-shaped distal and proximal openings 114 and 115 (FIG. 33), opposing square-shaped openings 116 and 117 (FIG. 34), opposing rectangular-shaped distal and proximal openings 118 and 119 (FIG. 35), opposing star-shaped distal and proximal openings 120 and 121 (FIG. 36), and opposing triangular-shaped distal and proximal openings 122 and 123 (FIG. 37).

Figure 38:
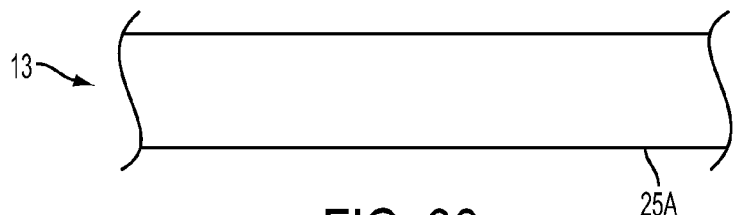
FIG. 38 is a side view of one embodiment of the arteriovenous shunt having a straight tubular configuration.
Figure 39:
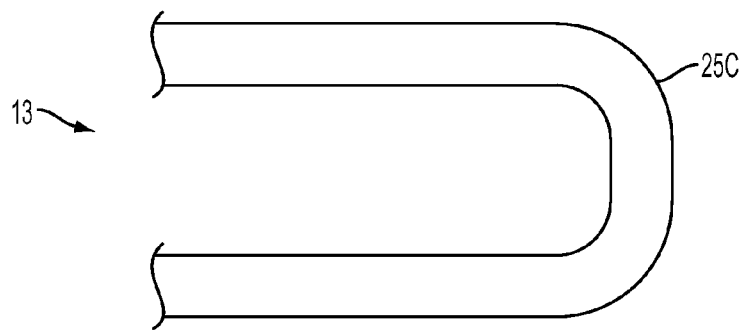
FIG. 39 is a side view of one embodiment of the arteriovenous shunt having a curved tubular configuration.
Figure 40:
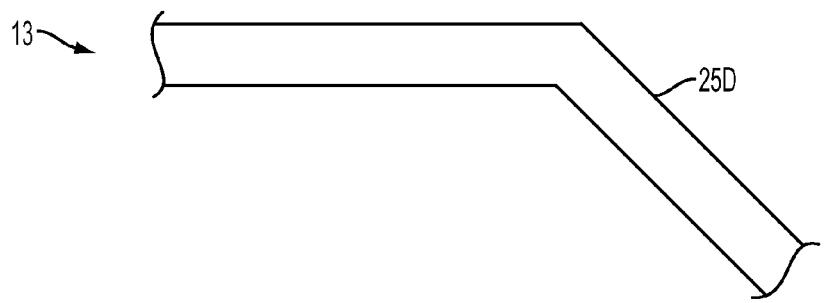
FIG. 40 is a side view of one embodiment of the arteriovenous shunt having a bent tubular configuration.

As shown in FIGS. 38-40, any of the tubular embodiments of the arteriovenous shunt 13 may have different configurations. For example, as noted above, arteriovenous shunt 13 may include a tubular-shaped arteriovenous shunt body 25A defining a generally straight tubular body (FIG. 38), while another arteriovenous shunt body may define a curved tubular-shaped shunt body 25C (FIG. 39) and yet another embodiment may include a bent-tubular shaped arteriovenous shunt body 25D defining a bent tubular-shape body (FIG. 40).

Figure 41:
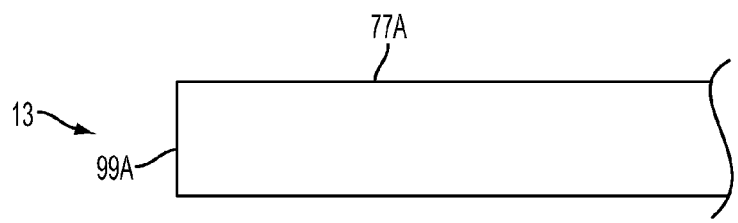
FIG. 41 is an enlarged side view of one embodiment of the arteriovenous shunt showing an end point with a flush configuration.
Figure 42:
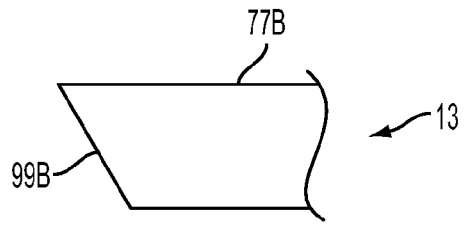
FIG. 42 is an enlarged side view of one embodiment of the arteriovenous shunt showing an end point with an angled configuration.
Figure 43:
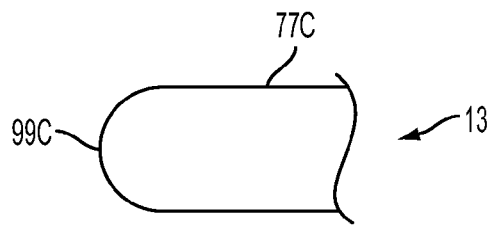
FIG. 43 is an enlarged side view of one embodiment of the arteriovenous shunt showing an end point with a curved configuration.
Figure 44:
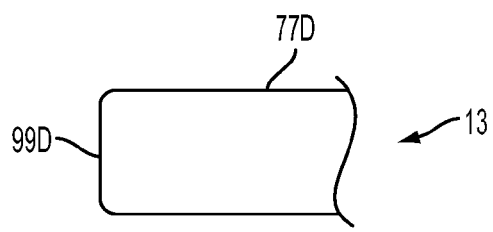
FIG. 44 is an enlarged side view of one embodiment of the arteriovenous shunt showing an end point with rounded edges.
Figure 45:
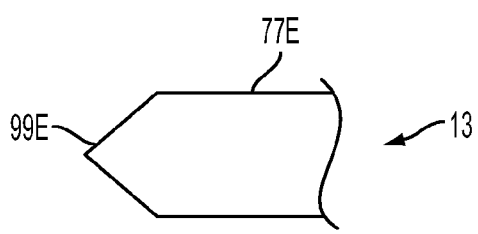
FIG. 45 is an enlarged side view of one embodiment of the arteriovenous shunt showing an end point with a pointed configuration.
Figure 46:
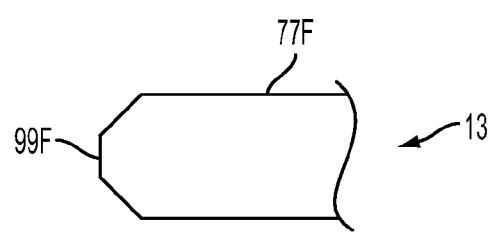
FIG. 46 is an enlarged side view of one embodiment of the arteriovenous shunt showing an end point with a trapezoidal configuration.
Figure 47:
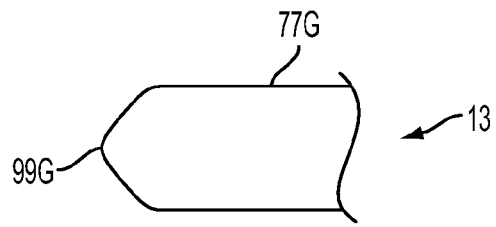
FIG. 47 is an enlarged side view of one embodiment of the arteriovenous shunt showing an end point with a dome-shaped configuration.
Figure 48:
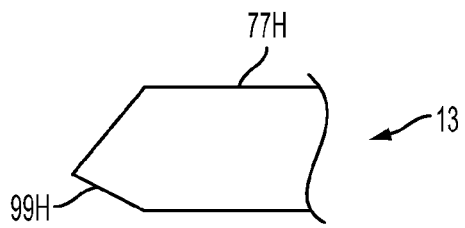
FIG. 48 is an enlarged side view of one embodiment of the arteriovenous shunt showing an end point with an asymmetrical pointed configuration.

Referring to FIGS. 41-48, any of the embodiments of the arteriovenous shunt 13 may have end points 77 in a variety of configurations. For example, as shown in FIG. 41, an arteriovenous shunt 13 may have an end point 77A defining a flush edge 99A, while another embodiment of the arteriovenous shunt 13 may have an end point 77B defining an angled edge 99B (FIG. 42). In addition, the arteriovenous shunt 13 may include an end point 77C defining a rounded edge 99C that may represent as much as a 180° arc in one embodiment (FIG. 43). With respect to other embodiments of the arteriovenous shunt 13, end point 77D may define a rectangular-shaped rounded edge 99D to minimize trauma during placement and retention of the arteriovenous shunt 13 (FIG. 44), end point 77E may define a pointed edge 99E (FIG. 45), end point 77F may define a trapezoidal-shaped edge 99F (FIG. 46), end point 77G may define a dome-shaped edge 99G (FIG. 47), and end point 77H may define an asymmetrically pointed edge 99H with the terminal point being angled in such a way that one base of the edge is a leading edge resulting in a smooth passage that provides a self-dilating effect as the arteriovenous shunt 13 passes through the tissue (FIG. 48).

In another aspect of the arteriovenous shunt 13, the arteriovenous shunts discussed above may be fabricated using different materials and manufacturing techniques. In one embodiment, the arteriovenous shunt 13 may be fabricated exclusively of a pure carbon material; however, other arteriovenous shunts may be fabricated using a substrate. For example, the arteriovenous shunt 13 may be fabricated from a substrate that is a polymer, elastomer, ceramic, or metal. In those embodiments of the arteriovenous shunt 13 made from a metal substrate, the composition of the metal substrate may be, but not limited to, gold, silver, copper, nickel, and/or titanium. In another embodiment, the substrate of the arteriovenous shunt 13 may be coated on inside and outside with a carbon material. Other embodiments of the arteriovenous shunt 13 may only have the inside of the substrate coated with the carbon material, while another embodiment may only have the outside of the substrate coated with the carbon material.

In yet another aspect, the arteriovenous shunt 13 may be fabricated from a polymer or a elastomer infused with carbon particles, while in other embodiments, the arteriovenous shunt 13 may be fabricated from a carbon substrate. Those embodiments of the arteriovenous shunt 13 made from the carbon substrate may be metal plated on the inside and outside surfaces of the arteriovenous shunt 13 or the metal may be plated exclusively inside or outside of the fluid path for the conduit. Other embodiments of the arteriovenous shunt 13 may be fabricated from a carbon substrate that has the metal vapor deposited on the inside and outside of the arteriovenous shunt 13, metal vapor deposited exclusively on the inside of the fluid path of the arteriovenous shunt 13, or metal vapor deposited exclusively on the outside of the fluid path of the arteriovenous shunt 13. Other fabrication techniques may include fabricating the arteriovenous shunt 13 by way of electrical discharge machining or a combination of electrical discharge machining with subsequent vapor deposition of carbon. Similarly, the arteriovenous shunt 13 may be fabricated by way of injection molding or a combination of injection molding with subsequent vapor deposition of carbon. Finally, other fabrication techniques may include stamping or a combination of stamping and subsequent vapor deposition of carbon as well as extrusion or a combination of extrusion and subsequent vapor deposition of carbon.

In preferred embodiments of the arteriovenous shunt 13, any of the shunts discussed above may be fabricated from materials comprising pure carbon or at least one carbon-based material such as a carbon fiber, carbon nanotubes, carbon preforms, or buckyballs. In especially preferred embodiments, the shunts may comprise functionalized carbon nanotubes. As used herein, the term "functionalized carbon nanotubes" refers to carbon nanotubes having one or both ends chemically attached to at least one base material. As such, a structure including functionalized carbon nanotubes would necessarily include at least one base material and a plurality carbon nanotubes attached to the at least one base material. In any respect, the carbon or carbon-based material is configured to inhibit growth of fibroblasts in the conduit. As used herein, "configured to inhibit growth of fibroblasts in the conduit" means that at least the surfaces of the body defining the inner walls of the conduit are made from or are covered with the carbon or carbon-based material. Though in some preferred embodiments the arteriovenous shunt 13 may be made exclusively of the materials comprising pure carbon or at least one carbon-based structure, in other preferred example embodiments, the materials may be present as fibroblast-inhibiting layers on inner walls of the conduit in communication with the fluid flowing through the conduit. The fibroblast-inhibiting layers may be attached to the inner walls and may intimately conform to the contours of the inner walls, such that fibroblast growth will be inhibited along the entire flow path of the conduit. The materials described with respect to these preferred embodiments may exhibit not only the flexibility desirable for drainage devices, but also a substantial anti-angiogenic activity against FGF2.

In one specific example, the base material may comprise a thin carbon scaffold consisting essentially of carbon fibers. Suitable carbon scaffolds in this regard include, for example, carbon veils, carbon-fiber tissues, and carbon-fiber mats. Though the carbon scaffold may be used alone, carbon nanotubes many be grown on the carbon scaffold to form in a fuzzy veil of carbon fibers. The term "fuzzy veil" refers to the ragged appearance of the original veil, tissue, or mat of carbon fibers under a microscope after nanotubes are grown on the carbon fibers. In still further examples, the fuzzy veil may be coated, for example by impregnation or other suitable technique, with a flexible and conformal polymer such as, for example, polymethylmethacrylate, to form a flexible composite.

In still further examples, the base material may comprise a two-dimensional carbon preform consisting essentially of a plurality of carbon-fiber tows. Likewise, carbon nanotubes may be grown on the carbon preform and optionally coated with a flexible polymeric material. In still further examples, the base material may comprise a carbon paper consisting essentially of carbon nanotubes and carbon nanofibers, prepared using a slurry technique analogous to slurry techniques commonly used in the art of cellulose paper manufacturing.

Referring to FIGS. 49-65, different embodiments of the thoracic catheter 14 will be discussed in greater detail. The thoracic catheter 14 is usually placed in thoracic surgery patients for drainage of fluids from the chest cavity which is often due to post-operative edema; however, prior art thoracic catheters can often clog and require flushing using either saline or some form of recombinant tissue plasminogen activator (t-PA). It has been found that fabricating thoracic catheters from carbon substantially inhibits or prevents clots from forming in the thoracic catheter 14, thereby promoting better patient care and reduced cost to providers since the cost for recombinant t-PA can be substantial.

Figure 49:
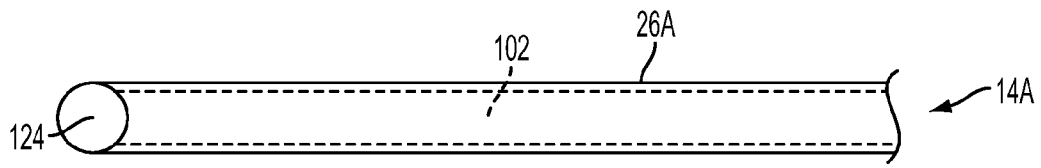
FIG. 49 is a side view of one embodiment of a thoracic catheter having a single lumen.
Figure 50:
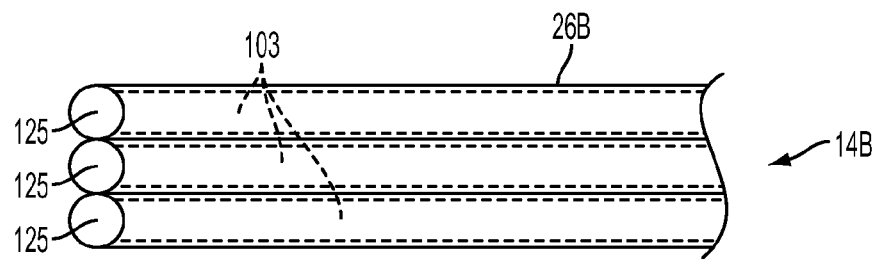
FIG. 50 is a side view of one embodiment of the thoracic catheter having multiple lumens.
Figure 51:
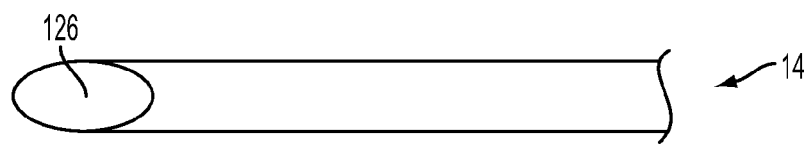
FIG. 51 is a side view of one embodiment of the thoracic catheter having oval openings.
Figure 52:
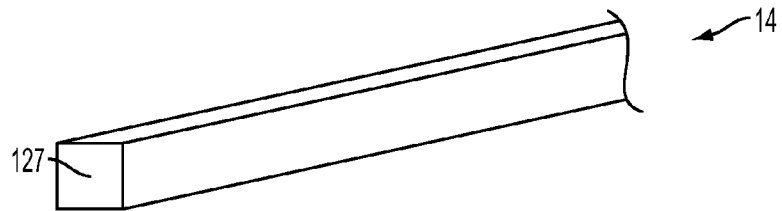
FIG. 52 is a side view of one embodiment of the thoracic catheter having square-shaped openings.
Figure 53:
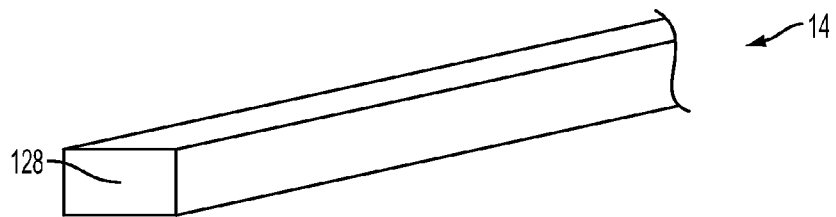
FIG. 53 is a side view of one embodiment of the thoracic catheter having rectangular-shaped openings.
Figure 54:
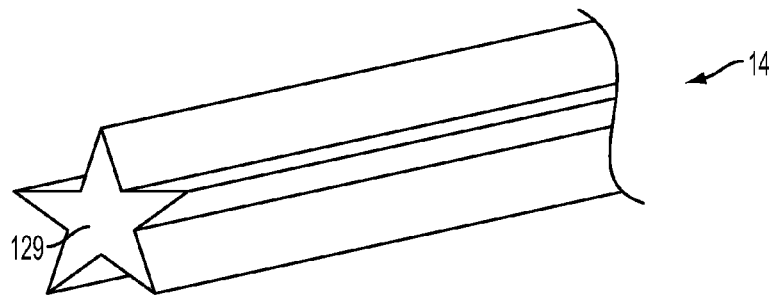
FIG. 54 is a side view of one embodiment of the thoracic catheter having star-shaped openings.

The embodiment of the thoracic catheter 14A shown in FIG. 49 includes a tubular-shaped thoracic catheter body 26A fabricated substantially of carbon that defines a circular distal opening 124 that communicates with a conduit 102 adapted to shunt fluid through tubular-shaped thoracic catheter body 26A, while the thoracic catheter 14B shown in FIG. 50 includes a multiple tubular-shaped thoracic catheter body 26B fabricated substantially of carbon that defines a plurality of conduits 101 that communicate with respective circular distal openings 125.

Figure 55:
FIG. 55 is a side view of one embodiment of the thoracic catheter having triangular-shaped openings.

Referring to FIGS. 51-55, any of the tubular embodiments of thoracic catheter 14 may have openings with different cross-sectional configurations. Although each of the embodiments for the thoracic catheter 14 has opposing distal and proximal openings, for purposes of illustration only the distal opening is shown. For example, thoracic catheter 14 may define opposing oval-shaped openings 126 (FIG. 51), opposing square-shaped openings 127 (FIG. 52), opposing rectangular-shaped openings 128 (FIG. 53), opposing star-shaped openings 129 (FIG. 54), and opposing triangular-shaped openings 130 (FIG. 55).

Figure 56:
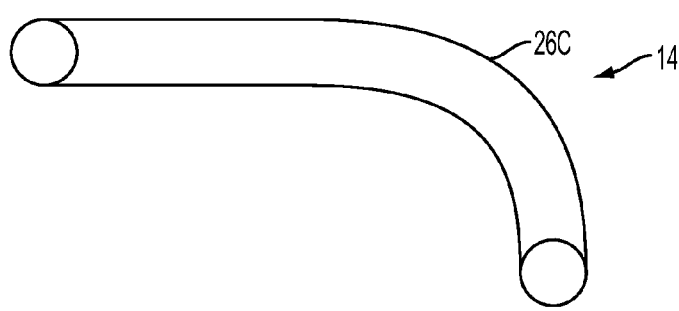
FIG. 56 is a side view of one embodiment of the thoracic catheter having a curved tubular configuration.
Figure 57:
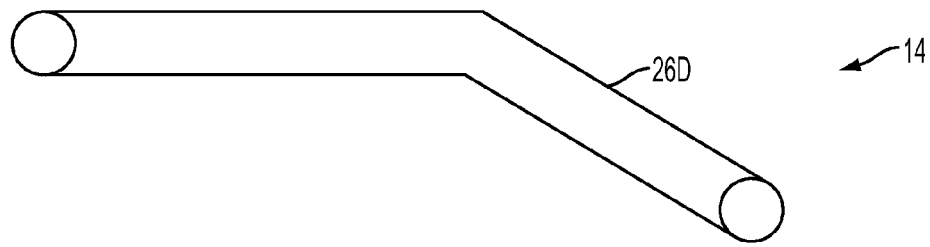
FIG. 57 is a side view of one embodiment of the thoracic catheter having a bent tubular configuration.

As shown in FIGS. 49, 55, and 56, any of the tubular embodiments of the thoracic catheter 14 may have different configurations. For example, as noted above, thoracic catheter 14 may include a tubular-shaped thoracic catheter body 26A defining a generally straight tubular body (FIG. 49), while another thoracic catheter 14 body may include a curved tubular-shaped thoracic catheter body 26C (FIG. 55) and yet another embodiment may include a bent tubular-shaped thoracic catheter body 26D (FIG. 56).

Figure 58:
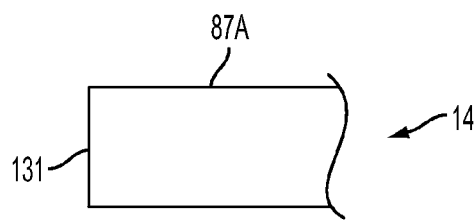
FIG. 58 is an enlarged side view of one embodiment of the thoracic catheter showing an end point with a flush configuration.
Figure 59:
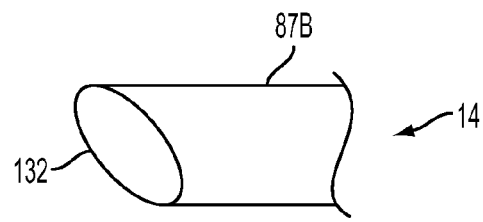
FIG. 59 is an enlarged side view of one embodiment of the thoracic catheter showing an end point with an angled configuration.
Figure 60:
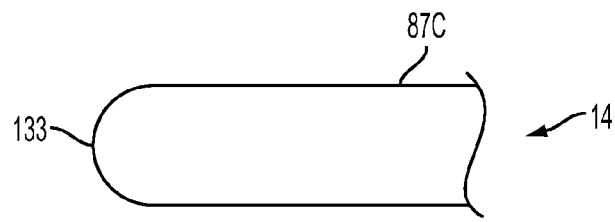
FIG. 60 is an enlarged side view of one embodiment of the thoracic catheter showing an end point with a curved configuration.
Figure 61:
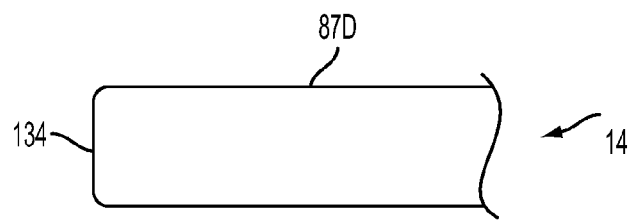
FIG. 61 is an enlarged side view of one embodiment of the thoracic catheter showing an end point with rounded edges.
Figure 62:
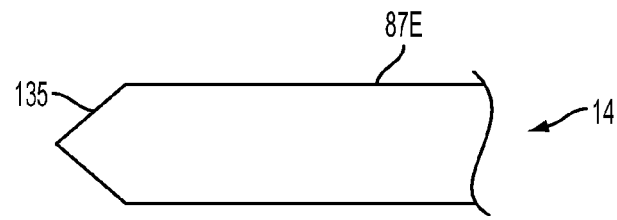
FIG. 62 is an enlarged side view of one embodiment of the thoracic catheter showing an end point with a pointed configuration.
Figure 63:
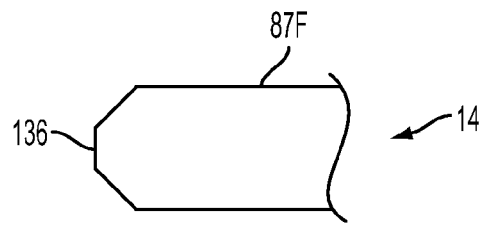
FIG. 63 is an enlarged side view of one embodiment of the thoracic catheter showing an end point with a trapezoidal configuration.
Figure 64:
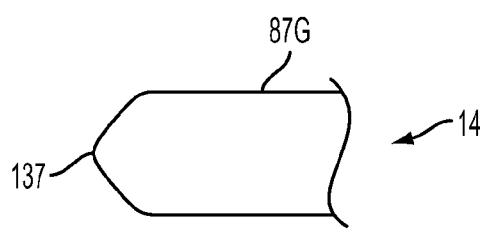
FIG. 64 is an enlarged side view of one embodiment of the thoracic catheter showing an end point with a dome-shaped configuration.
Figure 65:
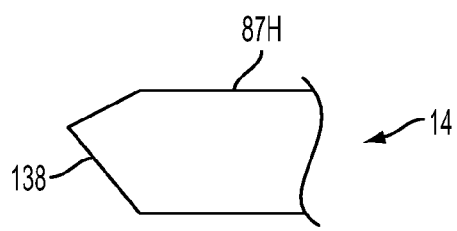
FIG. 65 is an enlarged side view of one embodiment of the thoracic catheter showing an end point with an asymmetrical configuration.

Referring to FIGS. 58-65 any of the embodiments of the thoracic catheter 14 may have end points 87 with various configurations. For example, as shown in FIG. 58, a thoracic catheter 14 may have an end point 87A defining a flush edge 131, while another embodiment of the thoracic catheter 14 may have an end point 87B defining an angled edge 132 (FIG. 59). In addition, the thoracic catheter 14 may include an end point 87C defining a rounded edge 133 that may represent as much as a 180° arc in one embodiment (FIG. 60). With respect to other embodiments of the thoracic catheter 14, end point 87D may define a rectangular-shaped rounded edge 134 to minimize trauma during placement and retention of the thoracic catheter 14 (FIG. 61), end point 87E may define a pointed edge 135 (FIG. 62), end point 87F may define a trapezoidal-shaped edge 136 (FIG. 63), end point 87G may define a dome-shaped edge 137 (FIG. 64), and end point 87H may define an asymmetrically pointed edge 138 (FIG. 65) with the terminal point being angled in such a way that one base of the edge is a leading edge resulting in a smooth passage and a self-dilating effect as the thoracic catheter 14 passes through the tissue.

In another aspect of the thoracic catheter 14, the thoracic catheters 14 discussed above may be fabricated using different materials and manufacturing techniques. In one embodiment, the thoracic catheter 14 may be fabricated exclusively of a pure carbon material; however, other thoracic catheters may be fabricated using a substrate. For example, the thoracic catheter 14 may be fabricated from a substrate that is a polymer, elastomer, ceramic, or metal. In those embodiments of the thoracic catheter 14 made from a metal substrate, the composition of the metal substrate may be, but not limited to, gold, silver, copper, nickel, and/or titanium. In another embodiment, the substrate of the thoracic catheter 14 may be coated on inside and outside with carbon material. Other embodiments of the thoracic catheter 14 may only have the inside of the substrate coated with carbon material, while another embodiment may only have the outside of the substrate coated with carbon material.

In yet another aspect, the thoracic catheter 14 may be fabricated from a polymer or an elastomer infused with carbon particles, while in other embodiments, the thoracic catheter 14 may be fabricated from a carbon substrate. Those embodiments of the thoracic catheter 14 made from a carbon substrate may be metal plated on the inside and outside surfaces of the thoracic catheter 14 or the metal may be plated exclusively inside or outside of the fluid path for the conduit. Other embodiments of the thoracic catheter 14 may be fabricated from a carbon substrate that has the metal vapor deposited on the inside and outside of the thoracic catheter 14, metal vapor deposited exclusively on the inside of the fluid path of the thoracic catheter 14, or metal vapor deposited exclusively on the outside of the fluid path of the thoracic catheter 14. Other fabrication techniques may include fabricating the thoracic catheter 14 by way of electrical discharge machining or a combination of electrical discharge machining with subsequent vapor deposition of carbon. Similarly, the thoracic catheter 14 may be fabricated by way of injection molding or a combination of injection molding with subsequent vapor deposition of carbon. Finally, other fabrication techniques may include stamping or a combination of stamping and subsequent vapor deposition of carbon as well as extrusion or a combination of extrusion and subsequent vapor deposition of carbon.

In preferred embodiments of the thoracic catheter 14, any of the catheters discussed above may be fabricated from materials comprising pure carbon or at least one carbon-based material such as a carbon fiber, carbon nanotubes, carbon preforms, or buckyballs. In especially preferred embodiments, the catheters may comprise functionalized carbon nanotubes. As used herein, the term "functionalized carbon nanotubes" refers to carbon nanotubes having one or both ends chemically attached to at least one base material. As such, a structure including functionalized carbon nanotubes would necessarily include at least one base material and a plurality carbon nanotubes attached to the at least one base material. In any respect, the carbon or carbon-based material is configured to inhibit growth of fibroblasts in the conduit. As used herein, "configured to inhibit growth of fibroblasts in the conduit" means that at least the surfaces of the body defining the inner walls of the conduit are made from or are covered with the carbon or carbon-based material. Though in some preferred embodiments the thoracic catheter 14 may be made exclusively of the materials comprising pure carbon or at least one carbon-based structure, in other preferred example embodiments, the materials may be present as fibroblast-inhibiting layers on inner walls of the conduit in communication with the fluid flowing through the conduit. The fibroblast-inhibiting layers may be attached to the inner walls and may intimately conform to the contours of the inner walls, such that fibroblast growth will be inhibited along the entire flow path of the conduit. The materials described with respect to these preferred embodiments may exhibit not only the flexibility desirable for drainage devices, but also a substantial anti-angiogenic activity against FGF2.

In one specific example, the base material may comprise a thin carbon scaffold consisting essentially of carbon fibers. Suitable carbon scaffolds in this regard include, for example, carbon veils, carbon-fiber tissues, and carbon-fiber mats. Though the carbon scaffold may be used alone, carbon nanotubes many be grown on the carbon scaffold to form in a fuzzy veil of carbon fibers. The term "fuzzy veil" refers to the ragged appearance of the original veil, tissue, or mat of carbon fibers under a microscope after nanotubes are grown on the carbon fibers. In still further examples, the fuzzy veil may be coated, for example by impregnation or other suitable technique, with a flexible and conformal polymer such as, for example, polymethylmethacrylate, to form a flexible composite.

In still further examples, the base material may comprise a two-dimensional carbon preform consisting essentially of a plurality of carbon-fiber tows. Likewise, carbon nanotubes may be grown on the carbon preform and optionally coated with a flexible polymeric material. In still further examples, the base material may comprise a carbon paper consisting essentially of carbon nanotubes and carbon nanofibers, prepared using a slurry technique analogous to slurry techniques commonly used in the art of cellulose paper manufacturing.

Referring to FIGS. 66-82, different embodiments of the central venous access device 15 will be discussed in greater detail. The central venous access device 15 may be placed in patients for continuous monitoring of cardiac efficiency and activity. It has been found that 5 million prior-art central venous access devices are placed in patients each year in the United States, and that occlusions occur frequently which can be caused by thrombosis.

Figure 66:
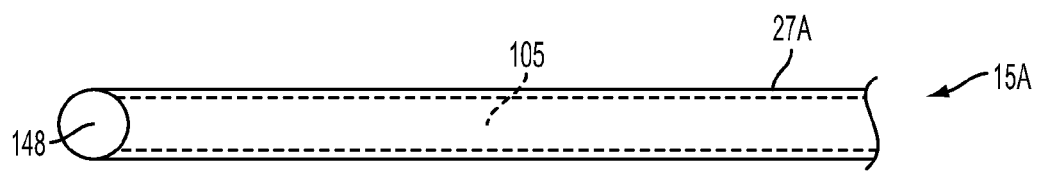
FIG. 66 is a side view of a central venous access device having a single lumen.
Figure 67:
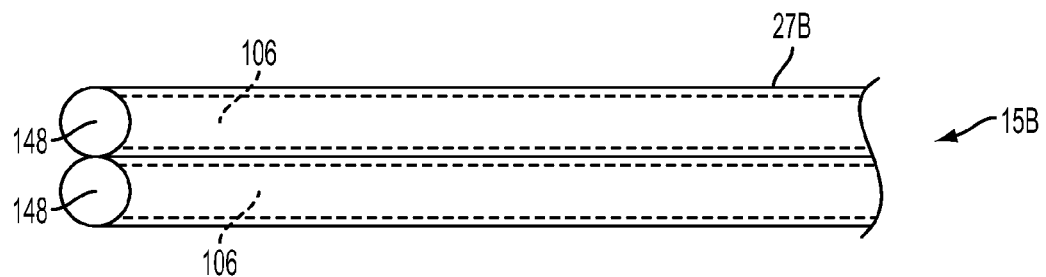
FIG. 67 is a side view of a central venous access device having multiple lumens.
Figure 68:
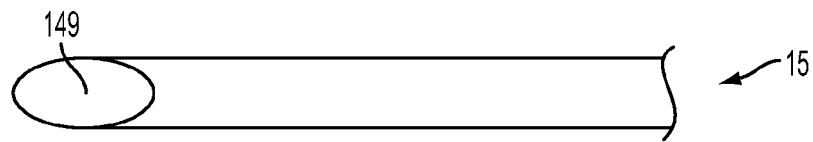
FIG. 68 is a side view of a central venous access device having oval-shaped openings.
Figure 69:
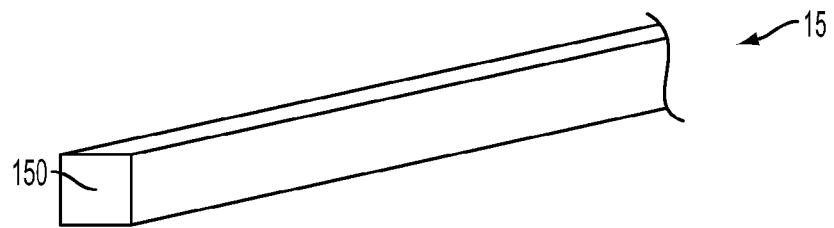
FIG. 69 is a side view of a central venous access device having square-shaped openings.
Figure 70:
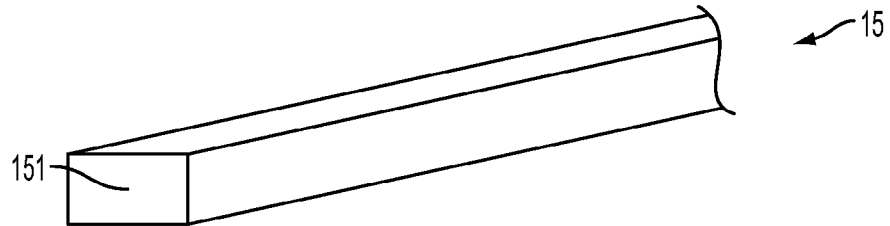
FIG. 70 is a side view of a central venous access device having rectangular-shaped openings.
Figure 71:
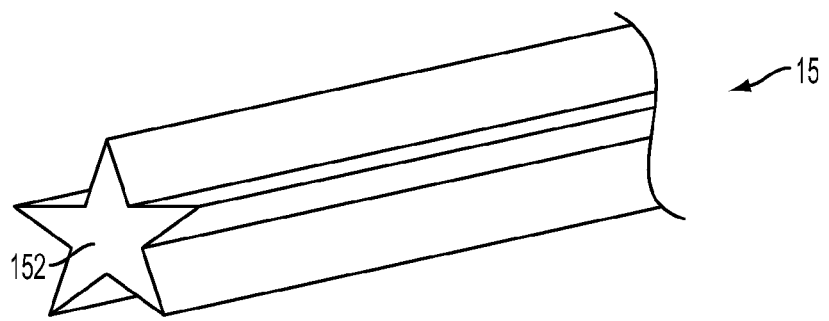
FIG. 71 is a side view of a central venous access device having star-shaped openings.

The embodiment of the central venous access device 15A shown in FIG. 66 includes a central venous access device body 27A that is tubular-shaped and is fabricated substantially of carbon that defines a circular distal opening 148 that communicates with a conduit 105 (shown in phantom) adapted to shunt fluid through central venous access device body 27A, while the central venous access device 15A shown in FIG. 67 includes a multiple tubular-shaped central venous access device body 27B fabricated substantially of carbon that defines a plurality of conduits 106 (shown in phantom) that communicate with respective circular distal openings 148.

Figure 72:
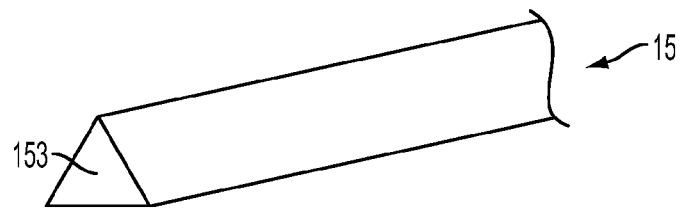
FIG. 72 is a side view of a central venous access device having triangular-shaped openings.

Referring to FIGS. 68-72, any of the tubular embodiments of central venous access device 15 may have openings with different cross-sectional configurations. Although each of the embodiments for the central venous access device 15 has opposing distal and proximal openings, for purposes of illustration only the distal opening is shown. For example, central venous access device 15 may define opposing oval-shaped openings 149 (FIG. 68), opposing square-shaped openings 150 (FIG. 69), opposing rectangular-shaped openings 151 (FIG. 70), opposing star-shaped openings 152 (FIG. 71), and opposing triangular-shaped openings 153 (FIG. 72).

Figure 73:
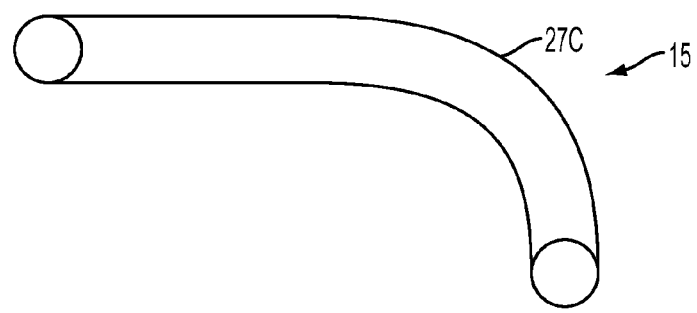
FIG. 73 is a side view of a central venous access device having a curved tubular configuration.
Figure 74:
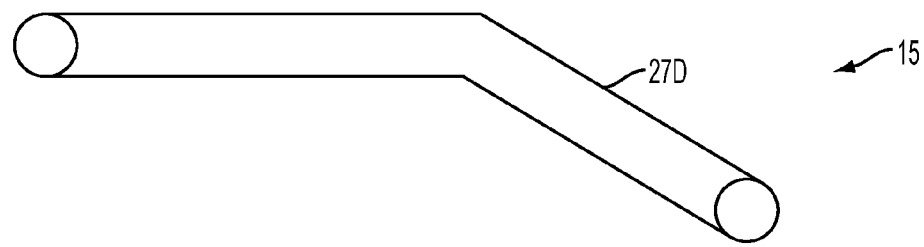
FIG. 74 is a side view of a central venous access device having a bent tubular configuration.

As shown in FIGS. 66, 73, and 74, any of the tubular embodiments of the central venous access device 15 may have different configurations. For example, as noted above, central venous access device 15 may include a central venous access device body 27A defining a generally straight tubular body (FIG. 66), while another central venous access device 27C may define a curved tubular-shaped central venous access device body (FIG. 73) and yet another embodiment may include a central venous access device body 27D defining a bent tubular-shaped body (FIG. 74).

Figure 75:
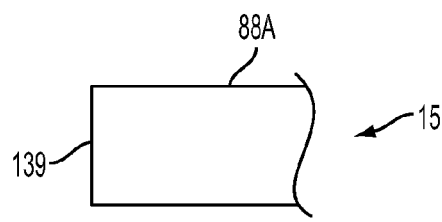
FIG. 75 is a side view of a central venous access device showing an end point with a flush configuration.
Figure 76:
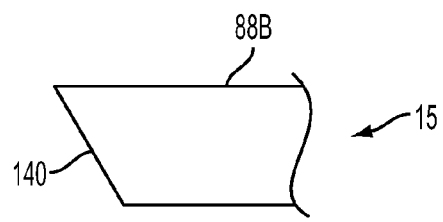
FIG. 76 is a side view of a central venous access device showing an end point with an angled configuration.
Figure 77:
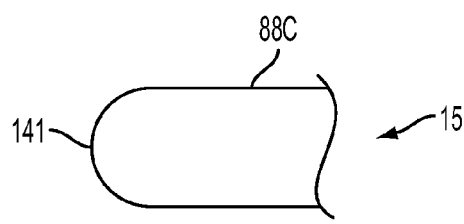
FIG. 77 is a side view of a central venous access device showing an end point with a curved configuration.
Figure 78:
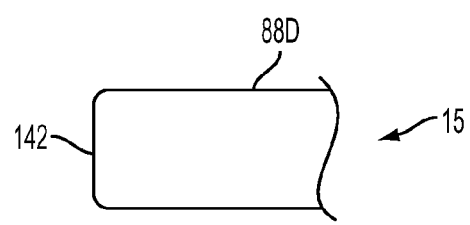
FIG. 78 is a side view of a central venous access device showing an end point with rounded edges.
Figure 79:
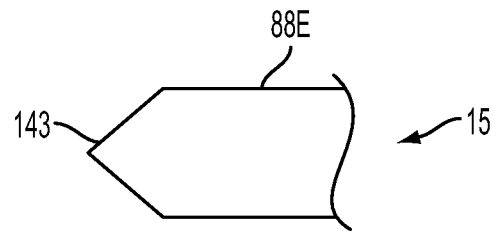
FIG. 79 is a side view of a central venous access device showing an end point with a pointed configuration.
Figure 80:
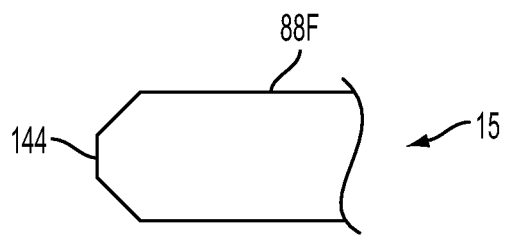
FIG. 80 is a side view of a central venous access device showing an end point with a trapezoidal configuration.
Figure 81:
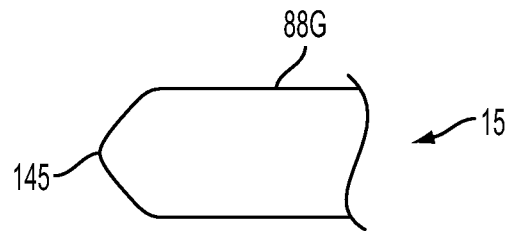
FIG. 81 is a side view of a central venous access device showing an end point with a dome-shaped configuration.

Referring to FIGS. 75-82 any of the embodiments of the central venous access device 15 may have end points 88 with various configurations. For example, as shown in FIG. 75, a central venous access device 15 may have an end point 88A defining a flush edge 139, while another embodiment of the central venous access device 15 may have an end point 88B defining an angled edge 140 (FIG. 76). In addition, the central venous access device 15 may include an end point 88C defining a rounded edge 141 that may represent as much as a 180° arc in one embodiment (FIG. 77). With respect to other embodiments of the central venous access device 15, end point 88D may define a rectangular-shaped rounded edge 142 to minimize trauma during placement and retention of the central venous access device 15 (FIG. 78), end point 88E may define a pointed edge 143 (FIG. 79), end point 88F may define a trapezoidal-shaped edge 144 (FIG. 80), end point 88G may define a dome-shaped edge 145 (FIG. 81), and end point 88H may define an asymmetrically pointed edge 138 with the terminal point being angled in such a way that one base of the edge is a leading edge resulting in a smooth passage and a self-dilating effect as the central venous access device 15 passes through the tissue (FIG. 82).

In another aspect of the central venous access device 15, the central venous access device 15 discussed above may be fabricated using different materials and manufacturing techniques. In one embodiment, the central venous access device 15 may be fabricated exclusively of a pure carbon material; however, other central venous access devices may be fabricated using a substrate. For example, the central venous access device 15 may be fabricated from a substrate that is a polymer, elastomer, ceramic, or metal. In those embodiments of the central venous access device 15 made from a metal substrate, the composition of the metal substrate may be, but not limited to, gold, silver, copper, nickel, and/or titanium. In another embodiment, the substrate of the central venous access device 15 may be coated on inside and outside with carbon material. Other embodiments of the central venous access device 15 may only have the inside of the substrate coated with carbon material, while another embodiment may only have the outside of the substrate coated with carbon material.

In yet another aspect, the central venous access device 15 may be fabricated from a polymer or an elastomer infused with carbon particles, while in other embodiments, the central venous access device 15 may be fabricated from a carbon substrate. Those embodiments of the central venous access device 15 made from a carbon substrate may be metal plated on the inside and outside surfaces of the central venous access device 15 or the metal may be plated exclusively inside or outside of the fluid path for the conduit. Other embodiments of the central venous access device 15 may be fabricated from a carbon substrate that has the metal vapor deposited on the inside and outside of the central venous access device 15, metal vapor deposited exclusively on the inside of the fluid path of central venous access device 15, or metal vapor deposited exclusively on the outside of the fluid path of central venous access device 15. Other fabrication techniques may include fabricating the central venous access device 15 by way of electrical discharge machining or a combination of electrical discharge machining with subsequent vapor deposition of carbon. Similarly, the central venous access device 15 may be fabricated by way of injection molding or a combination of injection molding with subsequent vapor deposition of carbon. Finally, other fabrication techniques may include stamping or a combination of stamping and subsequent vapor deposition of carbon as well as extrusion or a combination of extrusion and subsequent vapor deposition of carbon.

In preferred embodiments of the central venous access device 15, any of the venous access devices discussed above may be fabricated from materials comprising pure carbon or at least one carbon-based material such as a carbon fiber, carbon nanotubes, carbon preforms, or buckyballs. In especially preferred embodiments, the venous access devices may comprise functionalized carbon nanotubes. As used herein, the term "functionalized carbon nanotubes" refers to carbon nanotubes having one or both ends chemically attached to at least one base material. As such, a structure including functionalized carbon nanotubes would necessarily include at least one base material and a plurality carbon nanotubes attached to the at least one base material. In any respect, the carbon or carbon-based material is configured to inhibit growth of fibroblasts in the conduit. As used herein, "configured to inhibit growth of fibroblasts in the conduit" means that at least the surfaces of the body defining the inner walls of the conduit are made from or are covered with the carbon or carbon-based material. Though in some preferred embodiments the central venous access device 15 may be made exclusively of the materials comprising pure carbon or at least one carbon-based structure, in other preferred example embodiments, the materials may be present as fibroblast-inhibiting layers on inner walls of the conduit in communication with the fluid flowing through the conduit. The fibroblast-inhibiting layers may be attached to the inner walls and may intimately conform to the contours of the inner walls, such that fibroblast growth will be inhibited along the entire flow path of the conduit. The materials described with respect to these preferred embodiments may exhibit not only the flexibility desirable for drainage devices, but also a substantial anti-angiogenic activity against FGF2.

In one specific example, the base material may comprise a thin carbon scaffold consisting essentially of carbon fibers. Suitable carbon scaffolds in this regard include, for example, carbon veils, carbon-fiber tissues, and carbon-fiber mats. Though the carbon scaffold may be used alone, carbon nanotubes many be grown on the carbon scaffold to form in a fuzzy veil of carbon fibers. The term "fuzzy veil" refers to the ragged appearance of the original veil, tissue, or mat of carbon fibers under a microscope after nanotubes are grown on the carbon fibers. In still further examples, the fuzzy veil may be coated, for example by impregnation or other suitable technique, with a flexible and conformal polymer such as, for example, polymethylmethacrylate, to form a flexible composite.

In still further examples, the base material may comprise a two-dimensional carbon preform consisting essentially of a plurality of carbon-fiber tows. Likewise, carbon nanotubes may be grown on the carbon preform and optionally coated with a flexible polymeric material. In still further examples, the base material may comprise a carbon paper consisting essentially of carbon nanotubes and carbon nanofibers, prepared using a slurry technique analogous to slurry techniques commonly used in the art of cellulose paper manufacturing.

EXAMPLES

The following Examples are offered by way of illustration and are not meant to be limiting. Experiments were designed to evaluate growth of fibroblasts on various samples comprising carbon materials. The following materials were investigated:

Carbon Veil: a thin carbon scaffold consisting essentially of carbon fibers, also known as a carbon-fiber tissue;

Carbon Veil-CNT: carbon nanotubes grown on the carbon fibers of the Carbon Veil to produce the appearance of a fuzzy veil of carbon nanotubes over the carbon fibers;

Carbon Veil-PMMA: a carbon veil impregnated with polymethyl methacrylate (PMMA) to form a flexible composite;

Carbon Veil-CNT-PMMA: a fuzzy veil of carbon nanotubes grown on carbon fiber, which was subsequently impregnated with PMMA to form a flexible composite;

T300 Preform: a two-dimensional carbon preform made of T300 carbon-fiber tows (T300 is a trademark of Toray Carbon Fibers America, Inc.);

T300 Preform-CNT: a "fuzzy preform" made of carbon nanotubes grown on the T300 carbon fibers of a two-dimensional carbon preform;

CNT-Bucky: a carbon paper consisting essentially of functionalized carbon nanotubes and nanofibers and made using a slurry technique similar to the slurry techniques common in cellulose paper technology; and CNT-Bucky-Si-coating: a carbon paper consisting essentially of functionalized carbon nanotubes and nanofibers, which subsequently was coated with a polycarbosilane.

Fibroblast cells were seeded in 100-mm tissue-culture plates and were grown in Fibroblast Media (a mixture of F-12K with 10% fetal bovine serum and 1% penicillin streptomycin antibiotic) (F-12K is Kaighn's Modification of Ham's Medium, trademark of American Type Culture Collection) until confluent. Carbon samples cut to about 1 cm×1 cm were prepared beforehand and were sterilized for 1 hour in ethanol. The samples then were placed in six-well tissue-culture plates and were seeded with approximately 50,000 fibroblast cells. The cells were allowed to attach to the carbon samples over the course of 3 hours.

Then, fresh growth media was placed in the wells until the samples were completely covered. The samples were placed in an incubator (37° C., 5% $CO_2$) and were allowed to grow for a period of 1 week. The media was changed once every two days by replacing the old media with new media, and the samples were checked for contamination.

After one week, the samples were fixed in methanol-free formaldehyde for a fixing period of 20 minutes. Immediately after the fixing period, the formaldehyde was removed and the samples were washed twice with phosphate-buffered saline (PBS) for 5 minutes per wash.

Next, the samples were placed in a 0.001% solution of Triton X-100 to allow stain permeation. After stain permeation, the cells were washed again twice, for 5 min per wash. The samples then were soaked for 30 minutes in a solution containing Rhodamine phalloidin, a cell membrane stain. Again, the samples were washed twice for 5 min per wash. Then, the samples were soaked for 30 minutes in a solution containing 4',6-diamidino-2-phenylindole (DAPI), a nuclear stain. The final staining step consisted of washing the samples with PBS for 10 minutes and placing the samples in a solution of ProLong® Gold (available from Invitrogen), a solution that preserves the stained samples and prevents fluorescence loss.

The samples were observed under a Nikon® inverted microscope, and random images were captured at 10× magnification. Metamorph® cell-imaging software was used for imaging and cell counting. Six random images were counted, and the numbers of cells present in the images were averaged.

Optical microscopy imaging demonstrated that the fibroblast cells grew very well on Carbon Veil. Cell nuclei and actins were visibly attached to the carbon fibers of the Carbon Veil. The Carbon Veil was then coated with PMMA to make the veil very flexible and conformal. The fibroblast cells grew well on the PMMA polymer also. But when nanotubes were grown on the Carbon Veil to form Carbon Veil-CNT, the fibroblast cell growth was inhibited except in areas were nanotubes were missing or removed. On Carbon Veil-CNT-PMMA, however, cell proliferation was nearly eliminated.

The same experimental procedure was carried out on T300-based samples and similar results were obtained. Based on these consistent observations, it was considered that the presence of functionalized carbon nanotubes may be a key parameter for the inhibition of fibroblast cell growth. An additional sample was tested using CNT-Bucky, a carbon paper made on 100% functionalized carbon nanotubes, and no growth cell growth was observed on the sample. The CNT-Bucky was coated with polycarbosilane to produce a CNT-Bucky-Si-coated sample to simulate a thin surface layer of silicon. The CNT-Bucky-Si-coated was subjected to the fibroblast cell-growth procedure. After only one week of exposure time, the cell growth reached its maximum.

The results of the cell counts from optical microscopy conducted on the various materials is summarized in TABLE 1. TABLE 1 demonstrates that the fibroblast cells grew on all micrometric carbon surfaces but that the presence of carbon nanotubes was a common feature of the materials that apparently inhibited the proliferation of fibroblast cells. The highest proliferation of fibroblast cell growth occurred on the sample having a silicon coating covering the carbon structure.

Without intent to be bound by theory, it is believed silicon coating inherently lacks sufficient anti-angiogenic activity against FGF2, as required to inhibit fibroblast growth. TABLE 1 demonstrates also that, in all samples, most of the growth occurred during the first week. But with increasing incubation time, the rate of cell growth was observed to decrease.

TABLE 1

Observed fibroblast growth on various materials prepared according to the above procedures, after one week of incubation and after two weeks of incubation.

| Material | Fibroblast Cells per $cm^2$ After 1 week | Fibroblast Cells per $cm^2$ After 2 weeks |
| --- | --- | --- |
| Carbon Veil | 34000 | 66000 |
| Carbon Veil-PMMA | 26000 | 49000 |
| Carbon Veil-CNT | 2500 | 3100 |
| Carbon Veil-CNT-PMMA | 1300 | 300 |
| T300 Preform | 22000 | 28000 |
| T300 Preform-CNT | 3100 | 7500 |
| CNT-Bucky | 1300 | 0 |
| CNT-Bucky-Si-coated | 70000 | 73000 |

It should be understood from the foregoing that, while particular embodiments have been illustrated and described, various modifications can be made thereto without departing from the spirit and scope of the invention, as will be apparent to those skilled in the art. Such changes and modifications are within the scope and teachings of this invention as defined in the claims appended hereto.

What is claimed is:

1. A drainage device for draining a fluid from a patient during treatment of a medical condition, the drainage device comprising:
   a body having inner walls that define at least one conduit through the body from a proximal end of the body to a distal end of the body, the distal end being opposite the proximal end, the body comprising a carbon scaffold comprising carbon fibers optionally combined with a biocompatible polymer; and
   a layer of carbon nanotubes grown on the carbon fibers of the body inner walls, the resulting structure forming a carbon fuzzy veil,
   wherein:
   the carbon fuzzy veil resulting from the carbon nanotubes grown on the carbon scaffold is fibroblast-inhibiting relative to a carbon scaffold alone.

2. The drainage device of claim 1, wherein the carbon fuzzy veil has a ragged microscopic structure.

3. The drainage device of claim 1, wherein the carbon scaffold consists essentially of carbon fibers impregnated with polymethylmethacrylate.

4. The drainage device of claim 1, wherein: the drainage device is an ophthalmic shunt; the body is a tubular body having defined therein a proximal opening at the proximal end and a distal opening at the distal end.

5. The drainage device of claim 1, wherein:
   the drainage device is an ophthalmic shunt;
   the body has defined therein a proximal opening at the proximal end and a distal opening at the distal end; and
   the body comprises a plurality of flutes meeting at a central stem, each pair of adjacent flutes defining between the adjacent flutes a separate conduit and a slit in fluid communication with the separate conduit.

6. The drainage device of claim 1, wherein the drainage device is a hydrocephalus shunt and the body is a tubular body defining a closed distal end and a proximal opening, the proximal opening at the proximal end, the tubular body further defining a plurality of openings in fluid communication with the at least one conduit.

7. The drainage device of claim 1, wherein the drainage device is an arteriovenous shunt, and the body further defines a plurality of longitudinal flutes defined along the length of the body and extending from the proximal end to the distal end, each individual longitudinal flute of the plurality of longitudinal flutes having increasing width from the proximal end to the distal end.

8. The drainage device of claim 1, wherein the drainage device is a thoracic catheter and the body has a round cross-section defining a plurality of lumens in communication with multiple longitudinal flutes defined along the entire length of the body, the body further including a terminal point substantially perpendicular to the body and in communication with the plurality of lumens.

9. The drainage device of claim 1, wherein the drainage device is a central venous access device and the body comprises a plurality of lumens and a plurality of longitudinal flutes, the body further defining a proximal opening at the proximal end and a distal opening at the distal end, the proximal opening and the distal opening in fluid communication with the plurality of lumens.

10. The drainage device of claim 1, wherein the carbon scaffold consists essentially of carbon fibers and polymethylmethacrylate, wherein the carbon scaffold is impregnated with polymethylmethacrylate, or the carbon scaffold is built on polymethylmethacrylate or a polymethylmethacrylate substrate.

11. The drainage device of claim 1, wherein the carbon nanotubes cover the inner walls of the device body leaving substantially no uncovered surface.

12. The drainage device of claim 1, wherein the biocompatible polymer is selected from polymethylmethacrylate and polycarbosilane.

13. The drainage device of claim 1, wherein the carbon nanotubes are irregularly distributed over the inner walls of the device body.

14. A drainage device for draining a fluid from a patient during treatment of a medical condition, the drainage device comprising:
a body formed from a flexible composite and having inner walls that define at least one conduit through the body from a proximal end of the body to a distal end of the body, the distal end being opposite the proximal end, the flexible composite comprising a carbon scaffold consisting essentially of carbon fibers combined with a biocompatible polymer; and
a layer of carbon nanotubes grown on the carbon fibers of the body inner walls, the resulting structure forming a carbon fuzzy veil,
wherein:
the carbon fuzzy veil resulting from the carbon nanotubes grown on the carbon scaffold is fibroblast-inhibiting relative to a carbon scaffold alone.

15. The drainage device of claim 14, wherein:
the drainage device is an ophthalmic shunt;
the body is a tubular body having defined therein a proximal opening at the proximal end and a distal opening at the distal end.

16. The drainage device of claim 14, wherein:
the drainage device is an ophthalmic shunt;
the body has defined therein a proximal opening at the proximal end and a distal opening at the distal end; and
the body comprises a plurality of flutes meeting at a central stem, each pair of adjacent flutes defining between the adjacent flutes a separate conduit and a slit in fluid communication with the separate conduit.

17. The drainage device of claim 14, wherein the drainage device is a hydrocephalus shunt and the body is a tubular body defining a closed distal end and a proximal opening, the proximal opening at the proximal end, the tubular body further defining a plurality of openings in fluid communication with the at least one conduit.

18. The drainage device of claim 14, wherein the drainage device is an arteriovenous shunt, and the body further defines a plurality of longitudinal flutes defined along the length of the body and extending from the proximal end to the distal end, each individual longitudinal flute of the plurality of longitudinal flutes having increasing width from the proximal end to the distal end.

19. The drainage device of claim 14, wherein the drainage device is a thoracic catheter and the body has a round cross-section defining a plurality of lumens in communication with multiple longitudinal flutes defined along the entire length of the body, the body further including a terminal point substantially perpendicular to the body and in communication with the plurality of lumens.

20. The drainage device of claim 14, wherein the drainage device is a central venous access device and the body comprises a plurality of lumens and a plurality of longitudinal flutes, the body further defining a proximal opening at the proximal end and a distal opening at the distal end, the proximal opening and the distal opening in fluid communication with the plurality of lumens.

21. The drainage device of claim 14, wherein the carbon fuzzy veil has a ragged microscopic structure.

22. The drainage device of claim 14, wherein the carbon scaffold consists essentially of carbon fibers and polymethylmethacrylate, wherein the carbon scaffold is impregnated with polymethylmethacrylate, or the carbon scaffold is built on polymethylmethacrylate or a polymethylmethacrylate substrate.

23. The drainage device of claim 14, wherein the carbon nanotubes cover the inner walls of the device body leaving substantially no uncovered surface.

24. The drainage device of claim 14, wherein the biocompatible polymer is selected from polymethylmethacrylate and polycarbosilane.

25. The drainage device of claim 14, wherein the carbon nanotubes are irregularly distributed over the inner walls of the device body.

* * * * *